(12) United States Patent
Falla et al.

(10) Patent No.: US 7,390,873 B2
(45) Date of Patent: Jun. 24, 2008

(54) ANTIMICROBIAL CATIONIC PEPTIDES

(75) Inventors: Timothy J. Falla, San Jose, CA (US); Robert E. W. Hancock, Vancouver (CA); Monisha Gough, Vancouver (CA)

(73) Assignee: University of British Columbia, Vancouver (CA)

( * ) Notice: Subject to any disclaimer, the term of this patent is extended or adjusted under 35 U.S.C. 154(b) by 537 days.

(21) Appl. No.: 10/403,104

(22) Filed: Mar. 28, 2003

(65) Prior Publication Data

US 2004/0019181 A1 Jan. 29, 2004

Related U.S. Application Data

(60) Continuation of application No. 09/592,005, filed on Jun. 12, 2000, now abandoned, which is a division of application No. 08/702,054, filed on Aug. 23, 1996, now Pat. No. 6,191,254.

(60) Provisional application No. 60/002,687, filed on Aug. 23, 1995.

(30) Foreign Application Priority Data

Aug. 23, 1996 (WO) ................ PCT/IB96/00996

(51) Int. Cl.
*C07K 17/00* (2006.01)
*A61K 38/00* (2006.01)
*A61K 39/00* (2006.01)
*C12Q 1/18* (2006.01)

(52) U.S. Cl. ............ 530/327; 530/326; 530/328; 530/300; 435/32; 424/185.1; 514/13; 514/14; 514/15

(58) Field of Classification Search ........ 424/185.1; 435/849, 883, 884, 879, 922, 875, 32; 530/300, 530/350, 324–327, 328; 514/12, 13–15

See application file for complete search history.

(56) References Cited

U.S. PATENT DOCUMENTS

| | | | |
|---|---|---|---|
| 4,810,777 A | 3/1989 | Zasloff | 530/326 |
| 4,822,608 A | 4/1989 | Benton et al. | 424/98 |
| 5,028,530 A | 7/1991 | Lai et al. | 435/69.1 |
| 5,073,542 A | 12/1991 | Zasloff | 514/12 |
| 5,166,321 A | 11/1992 | Lai et al. | 530/324 |
| 5,202,420 A | 4/1993 | Zasloff et al. | 530/324 |
| 5,206,154 A | 4/1993 | Lai et al. | 435/69.7 |
| 5,208,220 A | 5/1993 | Berkowitz | 514/13 |
| 5,217,956 A | 6/1993 | Zasloff et al. | 514/13 |
| 5,235,038 A | 8/1993 | Blondelle et al. | 530/324 |
| 5,254,535 A | 10/1993 | Zasloff et al. | 514/12 |
| 5,324,716 A * | 6/1994 | Selsted et al. | 514/14 |
| 5,344,765 A | 9/1994 | Lai et al. | 435/69.7 |
| 5,357,044 A | 10/1994 | Lai et al. | 530/350 |
| 5,547,939 A * | 8/1996 | Selsted | 514/14 |
| 5,635,594 A * | 6/1997 | Lehrer et al. | 530/317 |
| 6,040,435 A | 3/2000 | Hancock | |

FOREIGN PATENT DOCUMENTS

| | | | |
|---|---|---|---|
| CA | A12040510 | | 10/1991 |
| EP | 0 356 409 | * | 2/1990 |
| WO | WO8911290 | * | 11/1989 |
| WO | WO9004407 | | 5/1990 |
| WO | WO9004408 | | 5/1990 |
| WO | WO9008552 | | 8/1990 |
| WO | WO9112270 | * | 2/1991 |
| WO | WO9108758 | | 6/1991 |
| WO | WO9112015 | * | 8/1991 |
| WO | WO9116918 | | 11/1991 |
| WO | WO9117760 | | 11/1991 |
| WO | WO9217195 | | 10/1992 |
| WO | WO9217197 | | 10/1992 |
| WO | WO92/22308 | | 12/1992 |
| WO | WO 92/22308 | | 12/1992 |
| WO | WO9222317 | | 12/1992 |
| WO | WO9301723 | | 2/1993 |
| WO | WO9305802 | | 4/1993 |
| WO | WO9311783 | | 6/1993 |
| WO | WO9324138 | | 12/1993 |
| WO | WO9404688 | * | 3/1994 |
| WO | WO 95/22338 | | 8/1995 |
| WO | WO95/22338 | | 8/1995 |

OTHER PUBLICATIONS

Yang et al. Internet. J. Antimicrob. Agents 27: 325-330, 2006.*

(Continued)

*Primary Examiner*—S. Devi
(74) *Attorney, Agent, or Firm*—DLA Piper US LLP

(57) ABSTRACT

A novel class of cationic peptides having antimicrobial activity is disclosed. These peptides can be encompassed by the formulas:

$X_1X_1PX_2X_3X_2P(X_2X_2P)_nX_2X_3(X_5)_o;$ (SEQ ID NO:23)

$X_1X_1PX_2X_3X_4(X_5)_rPX_2X_3X_3;$ (SEQ ID NO:24)

$X_1X_1X_3(PW)_uX_3X_2X_5X_2X_2X_5X_2(X_5)_o;$ and (SEQ ID NO:25)

$X_1X_1X_3X_3X_2P(X_2X_2P)_nX_2(X_5)_m;$ (SEQ ID NO:26)

wherein:
m is 1 to 5;
n is 1 or 2;
o is 2 to 5;
r is 0 to 8;
u is 0 or 1;
$X_1$ is Isoleucine, Leucine, Valine, Phenylalanine, Tyrosine, Tryptophan or Methionine;
$X_2$ represents Tryptophan or Phenylalanine
$X_3$ represents Arginine or Lysine;
$X_4$ represents Tryptophan or Lysine; and
$X_5$ represents Phenylalanine, Tryptophan, Arginine, Lysine, or Proline.

The invention also provides a method of producing a cationic peptide variant having antimicrobial activity.

10 Claims, 9 Drawing Sheets

OTHER PUBLICATIONS

Sitaram et al. Curr. Pharmaceut. Design 8: 727-742, 2002.*
McPhee et al. Comb. Chem. High Throughput Screen. 8: 257-272, May 2005 (abstract).*
Subbalakshmi et al. FEBS Lett. 395: 48-52, 2001.*
Friedrich et al. J. Biol. Chem. 276: 24015-24022, 2001.*
Staubitz et al. J. Peptide Sci. 7: 552-564, 2001.*
Friedrich et al. Antimicrob. Agents Chemother. 44: 2086-2092, 2000.*
Hancock et al. PNAS 97: 8856-8861, 2000.*
REW Hancock et al. In: Molecular Biology of Pseudomonads, International Symposium on Pseudomonads, 5th Meeting, Mol. Biol. Biotechnol., 1995, (Ed) T. Nakazawa et al. Chapter 38, pp. 441-450, 1996 ASM Press, Washington DC., 1996.*
J Rudinger. In: Peptide Hormones, (Ed) JA Parsons et al. pp. 1-7, University Park Press, Baltimore, 1976.*
E. Lazar et al. Mol. Cellular Biol. 8(3): 1246-1252, 1988.*
WH Burgess et al. J. Cell Biol. 111: 2129-2138, 1990.*
TJ Fall et al. J. Biol. Chem. 271(32): 19298019303, 1996.*
C Subbalakshmi et al. FEBS Lett. 395: 48-52, 1996.*
Del Sal et al. Biochem. Biophys. Res. Commun. 187: 467-472, abstract, 1992.*
Selsted et al. J. Biol. Chem. 67: 429-495, abstract, 1992.*
Romeo et al., "Bovine Neutrophil Antibiotic Peptides and Their Precursors: Structure and Role Innate Immunity," Croatica Chemica ACTA, vol. 68, No. 3, 1995 pp. 607-614.
Van Abel et al., "Synthesis and characterization of indolicidin, a tryptophan-rich antimicrobial peptide from bovine neutrophils", Int. J. Peptide Res.; 45, 1995, 401-409.
Uchida et al., "Antibacterial Activity of the Mammalian Host Defense Peptide, Indolicidin, and Its Fragments," Peptide Chemistry, 1995, N.Nishi (Ed.) (1996).
Romeo, D., et al., "Bovine Neutrophil Antibiotic Peptides and Their Precursors: Structure and Role in Innate Immunity," Croatica Chemica Acta, 1995, vol. 68, No. 3, pp. 607-614.
Van Abel, Robert J., et al., "Synthesis and Characterization of Indolicidin, a Tryptophan-Rich Antimocrobial Peptide from Bovine Neutrophils," International Journal of Peptide and Protein Research, 1995, vol. 45, pp. 401-409.
Selsted, Michael E., et al., "Indolicidin, a Novel Bachtericidal Tridecapeptide Amide from Neutrophils," Journal of Biological Chemistry, 1992, vol. 267, No. 7, pp. 4292-4295.
Harwig, Sylvia, et al., "Gallinacins: Cysteine-Rich Antimocrobial Peptides of Chicken Leukocytes," FEBS Letters, 1994, vol. 342, No. 3, pp. 281-285.
Del Sal, G., et al., "cDNA Cloning of the Neutrophil Bactericidal Peptide Indolicidin," Biochemical and Biophysical Research Communications, Aug. 31, 1992, vol. 187, No. 1, pp. 467-472.
Uchida, Yoshiki, et al., "Antibacterial Activity of the Mammalian Host Defense Peptide, Indolicidin, and Its Fragments," Peptide Chemistry, 1995, pp. 229-232.
Boman, Hans G., "Peptide Antibiotics and Their Role in Innate Immunity," Annual Review of Immunology, 1995, vol. 13, pp. 61-92.
Falla, Timothy J., et al., "Mode of Action of the Antimicrobial Peptide Indolicidin," Journal of Biological Chemistry, 1996, vol. 271, No. 32, pp. 19298-19303.
Falla, Timothy J., et al., "Improved Activity of a Synthetic Indolicidin Analog," Antimicrobial Agents and Chemotherapy, 1997, vol. 41, No. 4, pp. 771-775.
"Biologically Active and Amidated Cecropin Produced in a Baculovirus Expression System From a Fusion Construct Containing the Antibody-Binding Part of Protein A" The Biochemical Journal 280, Part 1: 219-224, 1991.

* cited by examiner

ANTIMICROBIAL CATIONIC PEPTIDES

CROSS-REFERENCE TO RELATED APPLICATIONS

This application is a continuation of U.S. Ser. No. 09/592,005, filed Jun. 12, 2000 (now abandoned, incorporated herein by reference), which is a divisional of U.S. Ser. No. 08/702,054, filed Aug. 23, 1996 (now U.S. Pat. No. 6,191,254, incorporated herein by reference), which claims priority under 35 U.S.C. § 119 to U.S. Ser. No. 60/002,687, filed Aug. 23, 1995.

FIELD OF THE INVENTION

The invention relates to peptides that have antimicrobial activity.

BACKGROUND OF THE INVENTION

Systemic diseases that are associated with pathogenic microorganisms or their toxins in the blood (e.g., septicemia) are a leading cause of death among humans. Gram-negative bacteria are the organisms most commonly associated with such diseases, and pathogenesis has been related in many cases to the release of a toxic outer membrane component termed endotoxin. However, gram-positive bacteria are an increasing cause of fatal infections. In addition, antibiotic resistance is becoming a major problem for all classes of antibiotics, and novel antibiotics are urgently needed.

Cationic peptides having antimicrobial activity have been isolated from a wide variety of organisms. In nature, such peptides provide a defense mechanism against o microorganisms such as bacteria and yeast. Generally, these cationic peptides are thought to exert their antimicrobial activity on bacteria by interacting with the cytoplasmic membrane to form channels or lesions. In gram-negative bacteria, they interact with surface lipopolysaccharide (LPS) to permeabilize the outer membrane, leading to self promoted uptake across the outer membrane and access to the cytoplasmic membrane. Examples of antimicrobial peptides include indolicidin, defensins, cecropins, and magainins.

SUMMARY OF THE INVENTION

The invention provides a novel class of isolated cationic peptides having antimicrobial activity. As a group, the peptides of the invention can be described by the following formulas:

$X_1X_1PX_2X_3X_2P(X_2X_2P)_nX_2X_3(X_5)_o;$ (SEQ ID NO:23)

$X_1X_1PX_2X_3X_4(X_5)_rPX_2X_3X_3;$ (SEQ ID NO:24)

$X_1X_1X_3(PW)_uX_3X_2X_5X_2X_2X_5X_2(X_5)_o;$ and (SEQ ID NO:25)

$X_1X_1X_3X_3X_2P(X_2X_2P)_nX_2(X_5)_m;$ (SEQ ID NO:26)

wherein:
  m is 1 to 5;
  n is 1 or 2;
  o is 2 to 5;
  r is 0 to 8;
  u is 0 or 1;
  $X_1$ is Isoleucine, Leucine, Valine, Phenylalanine, Tyrosine, Tryptophan or Methionine;
  $X_2$ represents Tryptophan or Phenylalanine;
  $X_3$ represents Arginine or Lysine;
  $X_4$ represents Tryptophan or Lysine; and
  $X_5$ represents Phenylalanine, Tryptophan, Arginine, Lysine, or Proline.

Various derivatives, analogues, conservative variations, and variants of the peptides described herein are included within the invention. Preferably, the peptide is amidated or carboxymethylated. Isolated nucleic acids encoding the peptides of the invention also are included. Examples of preferred peptides include those having the following amino acid sequences, as defined using the one-letter amino acid code:

| Sequence | ID |
|---|---|
| ILKKWPWWPWRRK | (SEQ ID NO:1); |
| ILKPWKWPWWPWRRKK | (SEQ ID NO:2); |
| ILKPWKWPWWPWRR | (SEQ ID NO:3); |
| ILPWKKWPWWRWRR | (SEQ ID NO:4); |
| ILKKWPWWPWRR | (SEQ ID NO:5); |
| ILPWKWPWWPWRKWR | (SEQ ID NO:6); |
| ILPWKWPWWPWRRWR | (SEQ ID NO:7); |
| ILPWKWPWWPWKKWK | (SEQ ID NO:8); |
| PWKWPWWPWRR | (SEQ ID NO:9); |
| ILPWKWPWRR | (SEQ ID NO:10); |
| ILPWKWPWWPWWPWRR | (SEQ ID NO:11); |
| ILPWKWPWWPWWKKPWRR | (SEQ ID NO:12); |
| ILPWICPWRPSKAN | (SEQ ID NO:13); |
| IVPWKWTLWPWRR | (SEQ ID NO:14); |
| TLPCLWPWWPWSI | (SEQ ID NO:15); |
| ILKKWPWWPWKIRR | (SEQ ID NO:17); |
| ILKKWPWWPWKWKK | (SEQ ID NO:18); |
| ILPWKWPWYVRR | (SEQ ID NO:19); |
| IKWPWYVWL | (SEQ ID NO:20); |
| ILPWKWFFPPWPWRR | (SEQ ID NO:21); |
| ILPWKWPPWPPWPWRR | (SEQ ID NO:22); |
| ILKKWPWWRWRR | (SEQ ID NO:27); |
| ILKKFPFFPFRRK | (SEQ ID NO:28); |
| ILKKFPFFPFKKK | (SEQ ID NO:29); |
| ILKKWAWWPWRRK | (SEQ ID NO:30); |
| ILKKWPWWAWRRK | (SEQ ID NO:31); |
| ILKKWPWWPWKKK | (SEQ ID NO:32); |
| ILRRWPWWPWRRR | (SEQ ID NO:33); |
| WWKKWPWWPWRRK | (SEQ ID NO:34); |
| FFKKWPWWPWRRK | (SEQ ID NO:35); |
| FFKKFPFFPFRRK | (SEQ ID NO:36); |
| FFKKFPFFPFKKK | (SEQ ID NO:37); |
| ILKKWPWWPWWPWRRK | (SEQ ID NO:38); |
| ILKKWPWWPWRWWRR | (SEQ ID NO:39); |

-continued

```
ILKKWPWWPWRRWWK          (SEQ ID NO:40);
ILKKWPWWPWPPRRK          (SEQ ID NO:41);
ILKKWPWWPWPPFRRK         (SEQ ID NO:42);
```

The invention also provides a method of inhibiting the growth of a bacterium (or bacteria) by contacting the bacterium with an inhibiting effective amount of one or more of the peptides of the invention, used simultaneously or sequentially. If desired, the peptide(s) can be used in combination with an antibiotic, simultaneously or sequentially. Such combination therapy may prove beneficial by a synergy occurring between the peptide and the antibiotic.

The invention also provides a method for inhibiting an endotoxemia or sepsis-associated disorder in a subject (e.g., a mammal such as a human) that has, or is at risk of having, such a disorder; the method entails administering to the subject a therapeutically effective amount of a peptide of the invention.

In addition, the invention provides a method for producing a cationic peptide variant having antimicrobial activity. This method entails: identifying the amino acid sequence of a reference cationic peptide having antimicrobial activity; producing an expression library encoding cationic peptide variants of the reference peptide (where a plurality of the variants each contain at least one substitution of an amino acid of the identified amino acid sequence); expressing the library in a plurality of host cells (thereby creating a plurality of clones); and isolating a clone that produces a cationic peptide variant having antimicrobial activity.

The invention provides several advantages. The peptides of the invention are compact and tend to have a unique polyproline type II extended helix structure that permits them to span the membrane with relatively few amino acids. The best peptides have very broad spectrum activity against antibiotic resistant bacteria, combined with activity against the medically important fungus, *Candida albicans*. These peptides also often possess the ability to work synergistically with antibiotics; in addition, they often possess anti-endotoxin activity. The peptides can be produced efficiently by recombinant DNA and protein chemical means. The invention also provides methods that permit both rationally designed and semi-random mutants of core structures (e.g., reference proteins) to be tested to permit variants within the formulas described herein to be produced and tested.

DETAILED DESCRIPTION OF THE INVENTION

Figure 1:
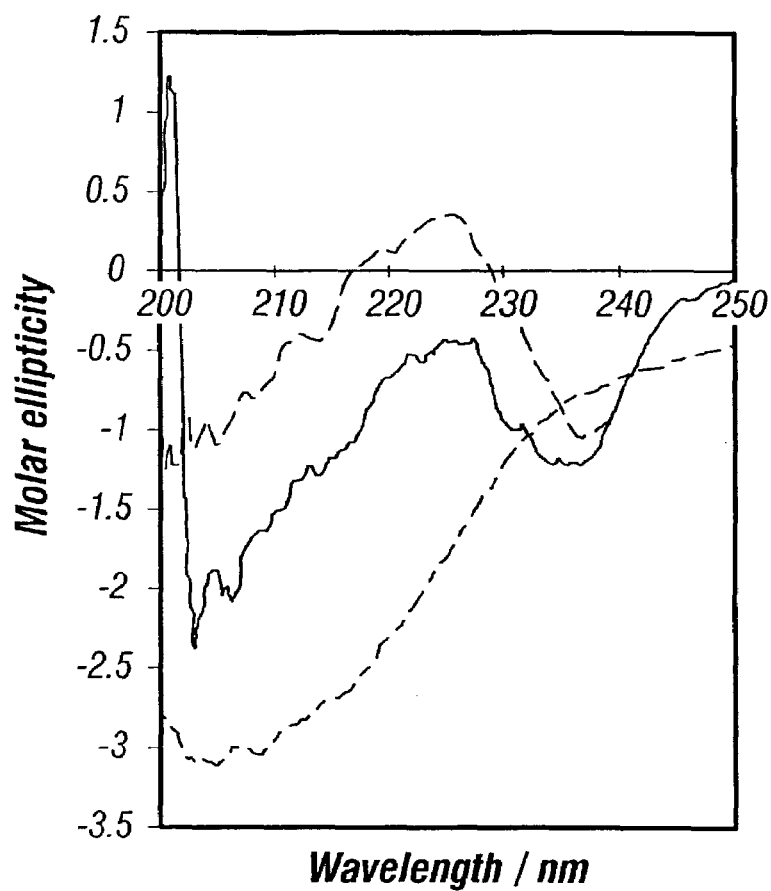
FIG. 1 shows CD spectra for CP-11 and indolicidin.

The present invention provides a novel class of cationic peptides (i.e., polypeptides) that have antimicrobial activity. These peptides are useful for inhibiting microbial infection or growth, as well reducing the effects of endotoxemia. The peptides can be used, for example, as preservatives in foods or cosmetics. Many of the peptides of the invention are synergistic with conventional antibiotics and can be used as an adjunct therapy. In addition, such peptides are useful as antifungal agents, antitumor agents, and/or antiviral agents.

The term "antimicrobial" as used herein means that the peptide destroys, or inhibits or prevents the growth or proliferation of, a microbe (e.g., a bacterium, fungus, and/or virus). Likewise, the term "antiviral" as used herein means that a peptide destroys, or inhibits or prevents the growth or proliferation of, a virus or a virus-infected cell. The term "antitumor" as used herein means that a peptide prevents, inhibits the growth of, or destroys, a tumor cell(s). Similarly, the term "antifungal" means that a peptide prevents, destroys, or inhibits the growth of a fungus.

As used herein, the term "cationic peptide" refers to a chain of amino acids that is 5 to 50 (preferably 9 to 25) amino acids in length. A peptide is "cationic" if it has a pKa greater than 9.0. Typically, at least four of the amino acid residues of the cationic peptide are positively charged residues, e.g., lysine and arginine. "Positively charged" refers to the side chain of an amino acid residue that has a net positive charge at pH 7.0.

As is described below, Applicants have devised formulas that encompass the isolated peptides of the invention. These peptides are represented by the amino acid sequences:

$X_1X_1PX_2X_3X_2P(X_2X_2P)_nX_2X_3(X_5)_o;$     (SEQ ID NO:23)

$X_1X_1PX_2X_3X_4(X_5)_rPX_2X_3X_3;$     (SEQ ID NO:24)

$X_1X_1X_3(PW)_uX_3X_2X_5X_2X_2X_5X_2(X_5)_o;$ and     (SEQ ID NO:25)

$X_1X_1X_3X_3X_2P(X_2X_2P)_nX_2(X_5)_m;$     (SEQ ID NO:26)

wherein:
   m is 1 to 5;
   n is 1 or 2;
   o is 2 to 5;
   r is 0 to 8;
   u is 0 or 1;
   $X_1$ is Isoleucine, Leucine, Valine, Phenylalanine, Tyrosine, Tryptophan or Methionine;
   $X_2$ represents Tryptophan or Phenylalanine;
   $X_3$ represents Arginine or Lysine;
   $X_4$ represents Tryptophan or Lysine; and
   $X_5$ represents Phenylalanine, Tryptophan, Arginine, Lysine, or Proline.

The term "isolated" as used herein refers to a peptide that is substantially free of other proteins, lipids, and nucleic acids (e.g., cellular components with which an in vivo-produced peptide would naturally be associated). Preferably, the peptide is at least 70%, 80%, or most preferably 90% pure by weight.

The invention also includes analogs, derivatives, conservative variations, and cationic peptide variants of the enumerated polypeptides, provided that the analog, derivative, conservative variation, or variant has a detectable antimicrobial activity. It is not necessary that the analog, derivative, variation, or variant have activity identical to the activity of the peptide from which the analog, derivative, conservative variation, or variant is derived.

A cationic peptide "variant" is an antimicrobial peptide that is an altered form of a referenced antimicrobial cationic peptide. For example, the term "variant" includes an antimicrobial cationic peptide produced by the method disclosed herein in which at least one amino acid of a reference peptide is substituted in an expression library. The term "reference" peptide means any of the antimicrobial cationic peptides of the invention (e.g., as defined in the above formulas), from which a variant, derivative, analog, or conservative variation is derived. Included within the term "derivative" is a hybrid peptide that includes at least a portion of each of two antimicrobial cationic peptides (e.g., 30-80% of each of two antimicrobial cationic peptides). Also included are peptides in which one or more amino acids are deleted from the sequence of a peptide enumerated herein, provided that the derivative has antimicrobial activity. For example, amino or carboxy terminal amino acids that are not be required for antimicrobial activity of a peptide can be removed. Likewise, additional derivatives can be produced by adding one or a few (e.g., less than 5) amino acids to an antimicrobial peptide without completely inhibiting the antimicrobial activity of the peptide. In addition, C-terminal derivatives, e.g., C-terminal methyl esters, can be produced and are encompassed by the invention.

The invention also includes peptides that are conservative variations of those peptides exemplified herein. The term "conservative variation" as used herein denotes a polypeptide in which at least one amino acid is replaced by another, biologically similar residue. Examples of conservative variations include the substitution of one hydrophobic residue, such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic for aspartic acid, or glutamine for asparagine, and the like. Neutral hydrophilic amino acids that can be substituted for one another include asparagine, glutamine, serine and threonine. The term "conservative variation" also encompasses a peptide having a substituted amino acid in place of an unsubstituted parent amino acid; preferably, antibodies raised to the substituted polypeptide also specifically bind the unsubstituted polypeptide.

The activity of the peptides of the invention can be determined using conventional methods known to those of skill in the art, such as in a "minimal inhibitory concentration (MIC)" assay described herein, whereby the lowest concentration at which no change in OD is observed for a given period of time is recorded as the MIC. Alternatively, a "fractional inhibitory concentration (FIC)" assay can be used to measure synergy between the peptides of the invention, or the peptides in combination with known antibiotics. FICs can be performed by checkerboard titrations of peptides in one dimension of a microtiter plate, and of antibiotics in the other dimension, for example. The FIC is a function of the impact of one antibiotic on the MIC of the other and vice versa. A FIC of 1 indicates that the influence of the compounds is additive and a FIC of less than 1 indicates that the compounds act synergistically.

Peptides of the invention can be synthesized by commonly used methods such as those that include t-BOC or FMOC protection of alpha-amino groups. Both methods involve stepwise synthesis in which a single amino acid is added at each step starting from the C terminus of the peptide (See, Coligan, et al., Current Protocols in Immunology, Wiley Interscience, 1991, Unit 9). Peptides of the invention can also be synthesized by the well known solid phase peptide synthesis methods such as those described by Merrifield, J. Am. Chem. Soc., 85:2149, 1962) and Stewart and Young, Solid Phase Peptides Synthesis, Freeman, San Francisco, 1969, pp. 27-62) using a copoly(styrene-divinylbenzene) containing 0.1-1.0 mMol amines/g polymer. On completion of chemical synthesis, the peptides can be deprotected and cleaved from the polymer by treatment with liquid HF-10% anisole for about ¼-1 hours at 0° C. After evaporation of the reagents, the peptides are extracted from the polymer with a 01% acetic acid solution, which is then lyophilized to yield the crude material. The peptides can be purified by such techniques as gel filtration on SEPHADEX® G-15 using 5% acetic acid as a solvent. Lyophilization of appropriate fractions of the column eluate yield homogeneous peptide, which can then be characterized by standard techniques such as amino acid analysis, thin layer chromatography, high performance liquid chromatography, ultraviolet absorption spectroscopy, molar rotation, or measuring solubility. If desired, the peptides can be quantitated by the solid phase Edman degradation.

The invention also includes isolated nucleic acids (e.g., DNA, cDNA, or RNA) encoding the peptides of the invention. Included are nucleic acids that encode analogs, mutants, conservative variations, and variants of the peptides described herein. The term "isolated" as used herein refers to a nucleic acid that is substantially free of proteins, lipids, and other nucleic acids with which an in vivo-produced nucleic acids naturally associated. Preferably, the nucleic acid is at least 70%, 80%, or preferably 90% pure by weight, and conventional methods for synthesizing nucleic acids in vitro can be used in lieu of in vivo methods. As used herein, "nucleic acid" refers to a polymer of deoxyribo-nucleotides or ribonucleotides, in the form of a separate fragment or as a component of a larger genetic construct (e.g., by operably linking a promoter to a nucleic acid encoding a peptide of the invention). Numerous genetic constructs (e.g., plasmids and other expression vectors) are known in the art and can be used to produce the peptides of the invention in cell-free systems or prokaryotic or eukaryotic (e.g., yeast, insect, or mammalian) cells. By taking into account the degeneracy of the genetic code, one of ordinary skill in the art can readily synthesize nucleic acids encoding the polypeptides of the invention. The nucleic acids of the invention can readily be used in conventional molecular biology methods to produce the peptides of the invention.

DNA encoding the cationic peptides of the invention can be inserted into an "expression vector." The term "expression vector" refers to a genetic construct such as a plasmid, virus or other vehicle known in the art that can be engineered to contain a nucleic acid encoding a polypeptide of the invention. Such expression vectors are preferably plasmids that contain a promoter sequence that facilitates transcription of the inserted genetic sequence in a host cell. The expression vector typically contains an origin of replication, and a promoter, as well as genes that allow phenotypic selection of the transformed cells (e.g., an antibiotic resistance gene). Various promoters, including inducible and constitutive promoters, can be utilized in the invention. Typically, the expression vector contains a replicon site and control sequences that are derived from a species compatible with the host cell.

Transformation or transfection of a host cell with a nucleic acid of the invention can be carried out using conventional techniques well known to those skilled in the art. For example, where the host cell is *E. coli*, competent cells that are capable of DNA uptake can be prepared using the $CaCl_2$, $MgCl_2$ or RbCl methods known in the art. Alternatively, physical means, such as electroporation or microinjection can be used. Electroporation allows transfer of a nucleic acid into a cell by high voltage electric impulse. Additionally, nucleic acids can be introduced into host cells by protoplast fusion, using methods well known in the art. Suitable methods for transforming eukaryotic cells, such as electroporation and lipofection, also are known.

"Host cells" encompassed by of the invention are any cells in which the nucleic acids of the invention can be used to express the polypeptides of the invention. The term also includes any progeny of a host cell. Preferred host cells of the invention include *E. coli, S. aureus* and *P. aeruginosa*.

Nucleic acids encoding the peptides of the invention can be isolated from a cell (e.g., a cultured cell), or they can be produced in vitro. A DNA sequence encoding a cationic peptide of interest can be obtained by: 1) isolation of a double-stranded DNA sequence from genomic DNA; 2) chemical manufacture of a nucleic acid such that it encodes the cationic peptide of interest; or 3) in vitro synthesis of a double-stranded DNA sequence by reverse transcription of mRNA isolated from a donor cell (i.e., to produce cDNA). Among the standard procedures for isolating cDNA sequences of interest is the formation of plasmid or phage containing cDNA libraries that are derived from reverse transcription of mRNA in donor cells that have a high level of genetic expression. When used in combination with polymerase chain reaction technology, even rare gene products can be cloned.

The invention also provides a method for inhibiting the growth of a bacterium by contacting the bacterium with an inhibiting effective amount of a peptide of the invention. The term "contacting" refers to exposing the bacterium to the peptide so that the peptide can inhibit, kill, or lyse bacteria. Preferably, the peptide is able to bind endotoxin (LPS), or permeabilize the outer membrane of a gram-negative bacterium. Contacting can occur in vitro, for example, by adding the peptide to a bacterial culture to test for susceptibility of the bacteria to the peptide. Alternatively, contacting can occur in vivo, for example by administering the peptide to a subject afflicted with a bacterial disorder, such as septic shock. "Inhibiting" or "inhibiting effective amount" refers to the amount of peptide that is sufficient to cause a bacteriostatic or bactericidal effect. Examples of bacteria that can be inhibited include *E. coli, P. aeruginosa, E. cloacae, S. typhimurium,* and *S. aureus*. The method for inhibiting the growth of bacteria can also include the contacting the bacterium with the peptide in combination with one or more antibiotics.

A peptide(s) of the invention can be administered to any host, including a human or non-human animal, in an amount effective to inhibit growth of a bacterium, virus, or fungus. Thus, the peptides are useful as antimicrobial agents, antiviral agents, and/or antifungal agents.

Any of a variety of art-known methods can be used to administer the peptide to a subject. For example, the peptide of the invention can be administered parenterally by injection or by gradual infusion over time. The peptide can be administered intravenously, intraperitoneally, intramuscularly, subcutaneously, intracavity, or transdermally. It may be formulated into liposomes to reduce toxicity or increase bio availability. Other preferred methods for delivery of the peptide include oral methods that entail encapsulation of the peptide in microspheres or proteinoids, aerosol delivery (e.g., to the lungs), or transdermal delivery (e.g., by iontophoresis or transdermal electroporation). Other methods of administration will be known to those skilled in the art.

Preparations for parenteral administration of a peptide of the invention include sterile aqueous or non-aqueous solutions, suspensions, and emulsions. Examples of non-aqueous solvents are propylene glycol, polyethylene glycol, vegetable oils (e.g., olive oil), and injectable organic esters such as ethyl oleate. Examples of aqueous carriers include water, saline, and buffered media, alcoholic/aqueous solutions, and emulsions or suspensions. Examples of parenteral vehicles include sodium chloride solution, Ringer's dextrose, dextrose and sodium chloride, lactated Ringer's, and fixed oils. Intravenous vehicles include fluid and nutrient replenishers, electrolyte replenishers (such as those based on Ringer's dextrose), and the like. Preservatives and other additives such as, other antimicrobial, anti-oxidants, cheating agents, inert gases and the like also can be included.

The invention provides a method for inhibiting an endotoxemia or septic shock (sepsis)-associated disorder by administering a therapeutically effective amount of a peptide of the invention to a subject who has, or is at risk of having, such a disorder. The term "inhibiting" means preventing or ameliorating a sign or symptoms of a disorder (e.g., endotoxemia). Examples of disease signs that can be ameliorated include an increase in a patient's blood level of TNF, fever, hypotension, neutropenia, leukopenia, thrombocytopenia, disseminated intravascular coagulation, adult respiratory distress syndrome, shock, and organ failure. Examples of patients who can be treated in the invention include those at risk for, or those suffering from, a toxemia, such as endotoxemia resulting from a gram-negative bacterial infection, venom poisoning, or hepatic failure. Other examples include patients infected with gram-positive bacteria, virus, or fungus. In particular, the invention is useful for treating patients who display signs of sepsis, or complain of symptoms of sepsis. Examples of candidate patients include those suffering from infection by *E. coli, Hemophilus influenza* B, *Neisseria meningitides,* staphylococci, or pneumococci. Other patients at risk for sepsis include those suffering from gunshot wounds, renal or hepatic failure, trauma, burns, immunocompromising infections (e.g., HIV infections), hematopoietic neoplasias, multiple myeloma, Castleman's disease or cardiac myxoma. Those skilled in the art of medicine can readily employ conventional criteria to identify appropriate subjects for treatment in accordance with the invention.

The term "therapeutically effective amount" as used herein for treatment of a patient afflicted with a disease or disorder means an amount of cationic peptide sufficient ameliorate a sign or symptom of the disease. For example, a therapeutically effective amount can be measured as the amount sufficient to decrease a subject's response to LPS or lessen any sign or symptom of sepsis. Preferably, the subject is treated with an amount of cationic peptide sufficient to reduce an LPS-induced increase in plasma TNF levels by at least 50%, and more preferably 90% or 100%. Generally, the optimal dosage of the peptide will depend upon the disorder and factors such as the weight of the patient. Nonetheless, suitable dosages can readily be determined by one skilled in the art. If desired, the effectiveness of treatment typically can be measured by monitoring the level of LPS or TNF in a patient. A decrease in serum LPS and TNF levels generally is correlated with amelioration of the disorder. Typically, a suitable dosage is 0.5 to 40 mg peptide/kg body weight, preferably 1 to 8 mg peptide/kg body weight.

If desired, a suitable therapy regime can combine administration of a peptide(s) of the invention with an inhibitor of TNF, an antibiotic, or both. For example, intervention in the role of TNF in sepsis, either directly or indirectly, such as by use of an anti-TNF antibody and/or a TNF antagonist, can prevent or ameliorate the signs of sepsis. An anti-TNF antibody, such as a monoclonal antibody that specifically binds TNF (e.g., as described by Tracey, et al. *Nature*, 330:662, 1987) is particularly preferred. The peptide(s), inhibitor(s), and/or antibiotic(s) can be administered, preferably, simultaneously, but may also be administered sequentially. Suitable antibiotics include aminoglycosides (e.g., gentamicin), beta-lactams (e.g., penicillins and cephalosporins), quinolones (e.g., ciprofloxacin), and novobiocin. Generally, the antibiotic is administered in a bactericidal amount. However, the peptide provides for a method of increasing antibiotic activity by permeabilizing the bacterial outer membrane and combinations involving peptide and a sub-inhibitory amount (an amount lower than the bactericidal amount) of antibiotic can be administered. Preferably, the cationic peptide and antibiotic are administered within 48 hours of each other (preferably 2-8 hours, most preferably, simultaneously). A "bactericidal amount" of antibiotic is an amount sufficient to achieve a bacteria-killing blood concentration in the patient receiving the treatment. In accordance with its conventional definition, an "antibiotic," as used herein, is a chemical substance produced by a microorganism that, in dilute solutions, inhibits the growth of, or kills, other microorganisms. Also encompassed by this term are synthetic antibiotics (e.g., analogs) known in the art.

The peptides of the invention can be used, for example, as preservatives or sterillants of materials susceptible to microbial or viral contamination. For example, the peptides can be used as preservatives in processed foods (e.g., to inhibit organisms such as *Salmonella, Yersinia*, and *Shigella*). If desired, the peptides can be used in combination with antibacterial food additives, such as lysozymes. The peptides of the invention also can be used as a topical agent, for example, to inhibit *Pseudomonas* or *Streptococcus* or kill odor-producing microbes (e.g., *Micrococci*). The optimal amount of a cationic peptide of the invention for any given application can be readily determined by one of skill in the art.

The invention also provides a method for producing an antimicrobial cationic peptide variant. This method entails identifying the amino acid sequence of a cationic peptide having antimicrobial activity (i.e., a reference peptide), producing an expression library encoding peptide variants of the reference peptide, where each variant contains at least one substitution (e.g., a random substitutions) of an amino acid(s) identified in the reference peptide; expressing the library in a plurality of host cells, thereby producing a plurality of clones; and isolating a clone that produces a peptide variant having antimicrobial activity. The invention also includes a cationic peptide variant produced by this method.

In this method, randomized nucleotide substitutions can be introduced into DNA encoding a reference cationic peptide having antimicrobial activity. Peptides having amino acid substitutions can thus be produced. For example, the example provided herein exemplifies randomization of a known antimicrobial peptide in order to produce variants having antimicrobial activity.

While any method of site directed mutagenesis can be used to produce cationic peptide variants, the preferred method utilizes DNA synthesis with a set of nucleotides in which each nucleotide stock, e.g., A,T,C, and G, contains a low percentage of the other nucleotides. For example, the adenosine stock contains about 0.5 to 5% of each of thymine, cytosine, and guanine. It is understood that the greater the level of "contaminating" nucleotides (i.e., T, C, and G in this example), the greater the number of nucleotide substitutions and corresponding amino acid substitutions per peptide.

Polymerase chain reaction (PCR) methods can be used to randomize specific regions of an oligonucleotide encoding a cationic peptide of the invention. PCR methods are well known in the art and are further illustrated in the Examples disclosed herein. The products of the PCR reactions can be pooled and gel purified prior to ligation into an expression vector to form a library. By expressing the library in a plurality of host cells (e.g., a strain of bacteria), a plurality of clones is produced. A clone that produces a cationic peptide variant having antimicrobial activity can readily be isolated by using a convention assay (e.g., a MIC assay as described herein and as known to those of skill in the art).

PCR primers used to amplify a nucleic acid encoding a variant cationic peptide typically are complementary to regions of the expression vector flanking the sequence encoding the variant cationic peptide.

Any nucleic acid sample, in purified or nonpurified form, can be used as a nucleic acid template for DNA synthesis, provided it contains a nucleic acid encoding the reference antimicrobial cationic peptide. Thus, the process can employ single stranded or double stranded DNA or RNA, such as messenger RNA. When RNA is used as a template, enzymes and conditions for reverse transcribing the RNA template to DNA are utilized. If desired, a DNA-RNA hybrid that contains one strand of each nucleic acid can be utilized. If desired, a mixture of nucleic acids can be employed, or the nucleic acids produced in a previous amplification reaction as described herein can be used with the same or different primers. It is not necessary that the nucleic acid to be amplified be present in a pure form; it can constitute a minor fraction of a complex mixture.

Where the nucleic acid encoding the reference protein is double-stranded, it is necessary to separate the strands of the nucleic acid in order to provide a nucleic acid template. This strand separation can be accomplished using any of various art-known denaturing conditions (e.g., physical, chemical, or enzymatic means). An example of a physical method of separating nucleic acid strands is heating the nucleic acid to about 80° to 105° C. for 1 to 10 minutes, followed by rapid cooling. Alternatively, strand separation can also be induced with an enzyme from the class of enzymes known as helicase or by the enzyme RecA, which has helicase activity. Reaction conditions suitable for strand separation of nucleic acids with helicases or RecA are known in the art (Kuhn Hoffmann-Berling *CSH-Quantitative Biology*, 43:63, 1978 and Radding, *Ann. Rev. Genetics*, 16:405-437, 1982).

Where the nucleic acid containing the sequence to be amplified is single stranded, its complement can be synthesized by using one or two oligonucleotide primers. If a single primer is utilized, a primer extension product can be synthesized in the presence of an agent for polymerization and the four common nucleotide triphosphates.

When complementary strands of nucleic acid or acids are separated, regardless of whether the nucleic acid was originally double or single stranded, the separated strands can be used as templates for the synthesis of additional nucleic acid strands. Typically, DNA synthesis occurs in a buffered aqueous solution, preferably at a pH of 7-9, most preferably about 8. Preferably, a molar excess (for genomic nucleic acid, usually about $10^8:1$ primer:template) of the two oligonucleotide primers is added to the buffer containing the separated template strands. In practice, the amount of primer added will generally be in molar excess over the amount of complementary strand (template) when the sequence to be amplified is contained in a mixture of complicated long-chain nucleic acid strands.

Typically, the deoxyribonucleotide triphosphates dATP, dCTP, dGTP, and dTTP are added to the synthesis mixture, either separately or together with the primers, in adequate amounts and the resulting solution is heated to about 90°-100° C. from about 1 to 10 minutes, preferably from 1 to 4 minutes. If desired, nucleotide analogs can be use din lieu of, in addition to, the common nucleotides. After this heating period, the solution typically is allowed to cool to a temperature that is optimal for primer hybridization (approximately 42° C.). To the cooled mixture is added an appropriate agent for effecting the primer extension reaction (called herein "agent for polymerization"), and the synthesis reaction is allowed to proceed under conditions known in the art. The agent for polymerization (e.g., a thermostable polymerase) may also be added together with the other reagents. This synthesis (or amplification) reaction can occur at any temperature at which agent for polymerization functions.

The agent for polymerization can be any compound (e.g., an enzyme) or system that functions to synthesize primer extension products. Suitable enzymes for this purpose include, for example, *E. coli* DNA polymerase I, Klenow fragment of *E. coli* DNA polymerase I, T4 DNA polymerase, polymerase muteins, reverse transcriptase, and other enzymes, especially heat-stable polymerases. The double-stranded molecule that results from DNA synthesis is then denatured, and the above-described synthesis process can be repeated on the resulting single-stranded nucleic acids. Additional agent for polymerization, nucleotides, and primers can be added if desired. The denaturing and DNA synthesis steps can be repeated if desired (as in conventional PCR methods).

Nucleic acids of the invention can be evaluated, detected, cloned, sequenced, and the like, either in solution or after binding to a solid support, by any method known in the art (e.g., PCR, oligomer restriction (Saiki, et al., *Bio/Technology*, 3:1008-1012, 1985), allele-specific oligonucleotide (ASO) probe analysis (Conner, et al., *Proc. Natl. Acad. Sci. USA*, 80:278, 1983), oligonucleotide ligation assays (OLAs) (Landegren, et al., *Science*, 241:1077, 1988), flourescent in situ hybridization (FISH), and the like).

In the present invention, a nucleic acid encoding a cationic peptide or peptide variants can be inserted into a recombinant "expression vector." The term "expression vector" refers to a plasmid, virus or other vehicle known in the art that can be manipulated by insertion or incorporation of a nucleic acid encoding a cationic peptide or variant. Typically, expression vectors are plasmids that contain a promoter for directing transcription of the inserted genetic sequence.

If desired, the expression vector can encode a "carrier peptide," which typically is produced as a fusion with the amino terminus of the peptide variant. Preferably, the carrier peptide is sufficiently anionic such that the positive charge associated with the cationic peptide is overcome and the resulting fusion peptide has a net charge that is neutral or negative. The anionic carrier peptide can correspond in sequence to a naturally-occurring protein or can be entirely artificial in design. Functionally, the carrier peptide may help stabilize the cationic peptide and protect it from proteases, although the carrier peptide need not be shown to serve such a purpose. Similarly, the carrier peptide may facilitate transport of the fusion peptide. Examples of carrier peptide that can be utilized include anionic pre-pro peptides and anionic outer membrane peptides. Preferred carrier peptides include, but are not limited to, glutathione-S-transferase (GST) (Smith et al., *Proc. Natl. Acad. Sci. USA*, 83:8703, 1986), protein A of *Staphylococcus aureus* (Nilsson, et al., *EMBO,* 4:1075, 1985; pRIT5 (Pharmacia)), two synthetic IgG-binding domains (ZZ) of protein A (Löwenadler, et al., *Gene,* 58:87, 1987) and outer membrane protein F of *Pseudomonas aeruginosa* (Duchene, et al, *J. Bacteriol*, 170:155, 1988). The invention is not limited to the use of these peptides as carriers; others suitable carrier peptides are known to those skilled in the art. Alternatively, the carrier peptide can be omitted altogether.

Any of various art-known methods for protein purification can be used to isolate the peptides of the invention. For example, preparative chromatographic separations and immunological separations (such as those employing monoclonal or polyclonal antibodies) can be used. Carrier peptides can facilitate isolation of fusion proteins that include the peptides of the invention. For example, glutathione-S-transferase (GST) allows purification with a glutathione agarose affinity column. When either Protein A or the ZZ domain from *Staphylococcus aureus* is used as the carrier protein, purification can be accomplished in a single step using an IgG-SEPHAROSE™ affinity column. The pOprF-peptide, which is the N-terminal half of the *P. aeruginosa* outer membrane protein F, can readily be purified because it is the prominent protein species in outer membrane preparations. If desired, the fusion peptides can be isolated by using reagents that are specifically reactive with (e.g., specifically bind) the cationic peptide of the fusion peptide. For example, monoclonal or polyclonal antibodies that specifically bind the cationic peptide can be used in conventional purification methods. Techniques for producing such antibodies are well known in the art.

In practicing the invention, it may be advantageous to include a "spacer DNA sequence" in the expression vectors. As used herein, "spacer DNA sequence" refers to any coding sequence located between the sequence encoding the carrier peptide and the sequence encoding the cationic peptide. While not wanting to be bound to a particular theory, it is believed that the spacer DNA sequence, when translated, can create a "hinge-like" region that allows the negatively charged residues of the anionic carrier peptide and the positively charged residues of the subject cationic peptide to interact, thereby inhibiting positive charge effects.

If desired, the spacer DNA sequence can encode a protein recognition site for cleavage of the carrier peptide from the fusion peptide. Examples of such spacer DNA sequences include, but are not limited to, protease cleavage sequences, such as that for Factor Xa protease, the methionine, tryptophan and glutamic acid codon sequences, and the pre-pro defensin sequence. Factor Xa is used for proteolytic cleavage at the Factor Xa protease cleavage sequence, while chemical cleavage by cyanogen bromide treatment releases the peptide at the methionine or related codons. In addition, the fused product can be cleaved by insertion of a codon for tryptophan (cleavable by o-iodosobenzoic acid) or glutamic acid (cleavable by *Staphylococcus* protease). Insertion of such spacer DNA sequences is not a requirement for the production of functional cationic peptides, such sequences can enhance the stability of the fusion peptide. The pre-pro defensin sequence is negatively charged; accordingly, it is envisioned within the invention that other DNA sequences encoding negatively charged peptides also can be used as spacer DNA sequences to stabilize the fusion peptide.

The following examples are intended to illustrate but not limit the invention. While they are typical of those that might be used, other procedures known to those skilled in the art may alternatively be used.

EXAMPLES

Example I

Synthesis of Cationic Peptides

Cationic peptides of the invention can be synthesized according to conventional protocols for protein synthesis (Merrifield, *J. Am. Chem. Soc.,* 85:2149, 1962; Stewart and Young, *Solid Phase Peptide Synthesis,* Freeman, San Francisco, 1969, pp 27-62). Generally, the resulting peptides are substantially pure, i.e., at least 70% pure. Typically, the resulting peptides are at least 80% pure, and more typically at least 99% pure. For example, the cationic peptides, termed CP-11 and CP-13 were synthesized by standard protein chemical procedures, and were at least 99% pure. In the examples provided below, indolicidin (an art-known antimicrobial agent) is used as a control. Indolicidin also was synthesized according to conventional methods, and it was at least 99% pure. The peptide CP-12 was approximately 80% pure, most likely because its sequence contained a larger number of positively charges residues in close proximity to tryptophans. Peptides CP-IA and CP-AA were synthesized by employing f-moc chemistry. Amino terminal modifications were made to peptides CP-11 and indolicidin; each was synthesized with the N-terminal amino acid in the D-form, thereby producing CP-11D and indolicidin-D. In addition, CP-11, CP-11D, indolicidin, and indolicidin-D each was methyl-esterified at the C-terminus, thereby producing CP-11, CP-11DC, indolicidin-C, and indolicidin-DC, respectively. Also, CP-11 was synthesized to contain o an amidated C-terminus, thereby producing CP-11N. Methods for producing peptides having an N-terminal amino acid, a methyl-esterified C-terminus, or an amidated C-terminus are well known in the art (Stewart and Young, supra; Kadaba, *Synthesis,* pp 628-631, 1992). The primary amino acid sequences of indolicidin, CP-11, CP-12, and CP-13 are shown in Table 1. For comparison, two peptides that lack significant antimicrobial activity, CP-IA and CP-AA, also were synthesized. CP-IA is expected to act synergistically with antibiotics as an antimicrobial.

TABLE 1

Synthetic Cationic Peptides

| Peptide | Amino acid sequence | |
|---|---|---|
| Indolicidin | ILPWKWPWWPWRR | (SEQ ID NO: 16) |
| CP-11 | ILKKWPWWPWRRK | (SEQ ID NO: 1) |
| CP-12 | ILKPWKWPWWPWRRKK | (SEQ ID NO: 2) |
| CP-13 | ILKKWPWWPWKWKK | (SEQ ID NO: 18) |
| CP-IA | ILPWKWPWYVRR | (SEQ ID NO: 19) |
| CP-AA | IKWPWYVWL | (SEQ ID NO: 20) |
| CP-16 | ILKKFPFFPFRRK | (SEQ ID NO: 28); |
| CP-24 | FFKKFPFFPFRRK | (SEQ ID NO: 36); |

Example II

Circular Dichroism Analysis

By combining an analysis of peptide structure with peptide function (e.g., antimicrobial activity), Applicants have devised a formula that defines the antimicrobial peptides of the invention (see below). Using Applicant's formula, a person of ordinary skill in the art can readily produce an antimicrobial peptide, such as a peptide specified herein, as well as those peptides that are encompassed by the formula, but not specified herein.

Structural analysis of indolicidin (a control) and CP-11 was performed using conventional circular dichroism (CD) analysis and a J-720 spectropolarimeter (Jasco, Japan). Suitable methods for CD have been described (see Haschmeyer and Haschmeyer, *Proteins, A Guide to Study by Physical and Chemical Methods,* Wiley-Interscience, pp 237-253; 1973). In this case, CD spectra were measured in 10 mM sodium phosphate buffer (pH 7.0), and in the presence or absence of 1-palmitoyl-2-oleoyl-sn-glycero-3-phosphocholine (POPC)/ 1-palmitoyl-2-oleoyl-sn-glycero-3-phosphoglycerol (POPG) (7:3) liposomes. Multilamellar liposomes were prepared by standard procedures (see, e.g., Mayer et al., Biochim. Biophys. Acta 817 (1985) 193-196) and extruded using an extruder device (Lipex Biomembranes, Vancouver, Canada) to produce unilamellar vesicles. The concentration of peptide and liposomes was 50 µM and 2 mM, respectively.

In the absence of liposomes, indolicidin and CP-11 exhibited CD spectra that were characteristic of an unordered structure (FIG. 1). In contrast, in the presence of liposomes (thereby mimicking the peptide's structure upon interaction with a cell membrane), the spectrum of indolicidin was characteristic of that produced by a poly-L-proline II extended helix structure. The spectrum was characterized by a minimum at 202 nm, a maximum at 226 nm, and a smaller minimum at 235 nm. This spectrum was only induced in the presence of negatively charges liposomes (i.e., such structures were not induced in the presence of POPC liposomes alone). This observation was not expected, because the low proline content of indolicidin would have been expected to preclude such a structure. Applicants' discovery that indolicidin formed a poly-L-proline II helix was critical in devising a formula for the design of cationic peptides.

Using circular dichroism, CP-11 produced a spectra (FIG. 1), which, although it had maximum and minimum at the same wavelengths as indolicidin, was distinct from indolicidin in that the minimum at 202 and 235 were reduced, and the maximum at 226 was increased in magnitude. Two peptides that lack significant antimicrobial activity, CP-IA and CP-AA (Table 1), also were analyzed by circular dichroism. Structural analysis of the non-antimicrobial peptides CP-IA and CP-AA revealed that certain motifs contribute significantly to the lipid-induced structure of the antimicrobial peptides. Both CP-IA and CP-AA remained unordered both in the absence of liposomes and in the presence of liposomes that were able to induce structure to the antimicrobial peptides (indolicidin and CP-11). Peptide IA differs from indolicidin in that it contains $Phe^9$ and $Val^{10}$ in lieu of $Trp^9$, $Pro^{10}$, and $Trp^{11}$ of indolicidin. Both CP-IA and CP-AA have significantly lower antimicrobial activities than does indolicidin (see below). Based on this structural analysis, it is expected that a poly-L-proline II helix structure contributes to antimicrobial activity.

Example III

Computer-based Modeling of Antimicrobial Peptides

Figure 2A:
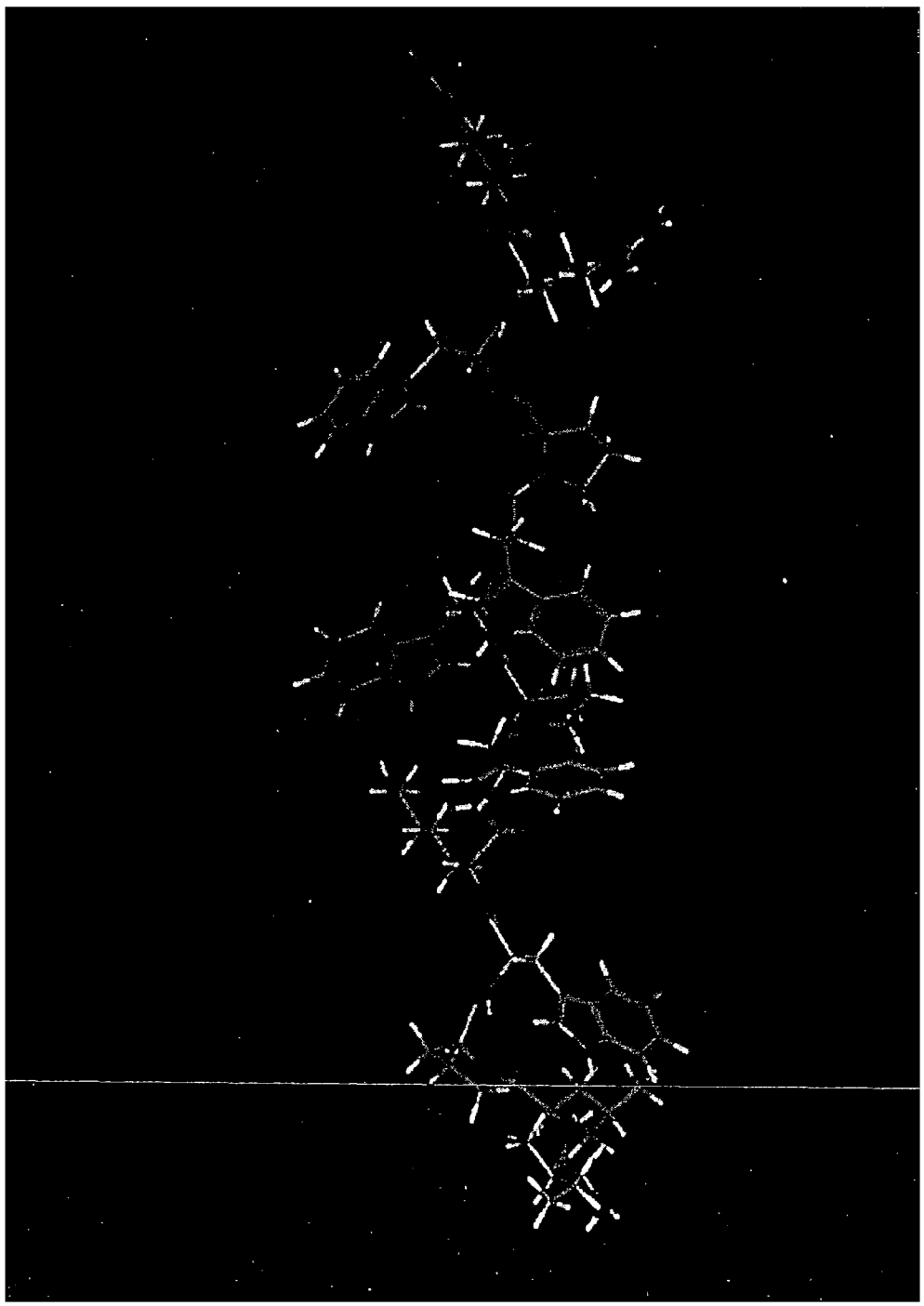
FIG. 2A shows the structure of indolicidin.
Figure 2B:
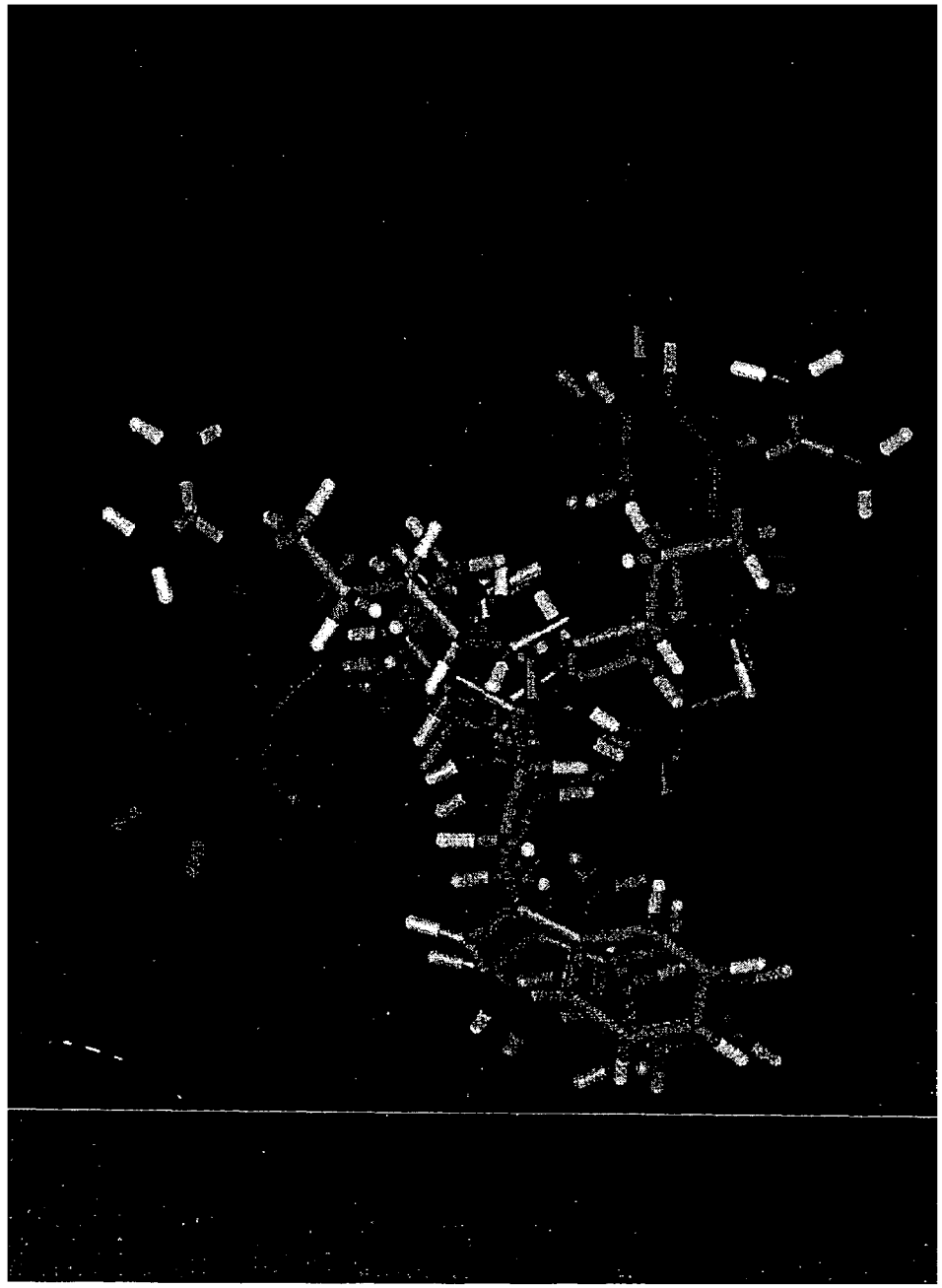
FIG. 2B shows a transverse view of the indolicidin structure.

Using InsightII (Biosym. Inc., San Diego, Calif.) molecular modeling software, indolicidin was modeled using the co-ordinates for a poly-L-proline II helix. The resulting structure is shown in FIG. 2A. These data show that the peptide in this form is approximately 40 Å in length. Also, $Trp^6$, $Trp^8$, $Trp^9$ and $Trp^{11}$ are all aligned in the same plane (FIG. 2B), as opposed to $Trp^4$, which is aligned in the opposite plane. Using CP-11 and the coordinates for a poly-L-proline II helix, computer modeling showed that all of the tryptophans of CP-11 were aligned in a single plane. Because CP-11 is a more potent antimicrobial peptide than is indolicidin (see below), this structural analysis combined with the functional analysis, suggests that formation of an amphipathic structure, as in CP-11 is desirable.

Example IV

Assay for Antimicrobial Activity

Any of the art-known methods for measuring antimicrobial activity of peptides can be used in characterizing the peptides of the invention. In these examples, conventional methods were used to determine the minimal inhibitory concentration (MIC) of a peptide in a liquid medium (Amsterdam. Antibiotics in Laboratory Medicine, Williams and Wilkins, Baltimore (1991) 72-78). Briefly, overnight cultures of the test organisms (described below) were diluted to produce an inoculum containing approximately $10^4$ to $10^5$ organisms. The inoculum size was confirmed by counting the number of organisms on plates that were inoculated at the same time as the liquid cultures.

The concentration of peptide was measured by assaying for free amino groups using a dinitrophenylation assay, with polymyxin B serving as a standard. Doubling dilutions of peptide were performed (32 µg/ml-0.25 µg/ml) in 100 µl volumes in a 96-well mictrotiter plate, and all wells were subsequently inoculated with the diluted culture of the test organism. After 24 hours of incubation at 37° C., the assay was read. The MIC value is the concentration of peptide at which the growth of the test organism was reduced by 50%. The number of cells in the culture inoculum was calculated from the plate count after incubating the plate for 24 hours at 37° C. The medium used for cell culture and dilution in this assay was Luria broth (LB). Each peptide was tested three times against each organism, and the MIC values presented below are the mean values of the three experiments. The test organisms used in the MIC assays are listed in Table 2.

TABLE 2

Test strains used for MIC determination

| Strain Number | Organism | Source |
|---|---|---|
| UB1005 | E. coli | D. Clark |
| 14028S | Salmonella typhimurium | Defensin sensitive (F. Heffron) |
| C621 | Staphylococcus epidermidis | Clinical isolate (D. Speert) |
| RN4220 | Staphylococcus aureus | ATCC 25293 |
| C627 | Candida albicans | UBC Microbiology department collection |
| K799 | Pseudomonas aeruginosa | W. Zimmerman |

See Piers et al., *Antimicrob. Agents. Chemother.*, 38:2311-2316, 1994 for a citation to the Gram negative bacterial strains.

MIC values for each of the peptides are shown in Table 3. These data show that the cationic peptide CP-11 had greater antimicrobial activity against gram-negative bacteria and the yeast *Candida albicans* than did indolicidin. Similarly, CP-13 displayed greater antimicrobial activity against gram-negative bacteria than did indolicidin. The peptide CP-16, which had Phenylalanine substituted for Tryptophan but otherwise had the same sequence as CP-13, was equivalent to this peptide in activity against *S. aureus*, showing that the peptides of the invention did not need to be Tryptophan-rich. A further substitution of the first two residues in CP-24 for the hydrophobic amino acid phenylalanine led to a peptide that was superior to indolicidin and better than CP-13 against *S. aureus*.

MIC values also were determined for various derivatives of indolicidin, CP-11, and CP-13. As described above the C-terminus of indolicidin and CP-11 was chemically converted to a methyl-ester, thereby producing indolicidin-C and CP-11C. The amidated derivative of CP-11, CP-11N, was made by f-moc chemistry. In the case of indolicidin, methyl esterification reduced the MIC for all organisms except *P. aeruginosa* and *C. albicans*. In the case of CP-11, the methyl esterification reduced the MIC values for all organisms except *S. aureus* SAP0017 and *C. albicans*. CP-11C produced MIC values 8 fold lower than indolicidin for the gram-negative organisms and *C. albicans*. CP-11 and CP-11C are particularly valuable for their antimicrobial activity against *P. aeruginosa*. These results are attributed to the increase in positive charge and orientation of the hydrophobic residues of CP-11 and its derivatives. The peptide having the most potent antimicrobial activity, CP-11C, exhibited MIC values of 1-8 µg/ml for all of the organisms tested.

TABLE 3

MIC values for synthetic peptides
MIC µg/ml

| | E. coli | P. aeruginosa | S. typhimurium | S. aureus | S. epidermidis | C. albicans |
|---|---|---|---|---|---|---|
| Indolicidin | 16 | >32 | 8 | 8 | 8 | >32 |
| CP-11 | 4 | 16 | 2 | 16 | 2 | 8 |
| CP-13 | 8 | >32 | 4 | >32 | 4 | >32 |
| CP-16 | 16 | 64 | 16 | 16 | | |
| CP-24 | 8 | 32 | 8 | 8 | | |
| CP-IA | >32 | >32 | >32 | >32 | >32 | >32 |
| CP-AA | >32 | >32 | >32 | >32 | >32 | >32 |
| Indolicidin-C | 4 | >32 | 2 | 4 | 1 | >32 |
| CP-11C | 2 | 8 | 1 | 8 | 1 | 8 |
| Indolicidin-D | 8 | >32 | 4 | 4 | 2 | >32 |
| CP-11D | 4 | 4 | 2 | 4 | 2 | 8 |
| Indolicidin-DC | 4 | >32 | 4 | 8 | 2 | >32 |

TABLE 3-continued

MIC values for synthetic peptides
MIC µg/ml

| | E. coli | P. aeruginosa | S. typhimurium | S. aureus | S. epidermidis | C. albicans |
|---|---|---|---|---|---|---|
| CP-11DC | 4 | 4 | 2 | 4 | 2 | 8 |
| CP-11N | 1 | | | >32 | 8 | |

Indolicidin, indolicidin C, and CP-11 also were synthesized such that the N-terminal amino acid was in the D form, thereby producing indolicidin-D, indolicidin-DC and CP-11C, respectively. The N-terminal modification of CP-11 (creating CP-11D) decreased the MIC value for the peptide. The MIC for CP-11DC was comparable to the MIC for CP-11D. Indolicidin-D exhibits MIC values that are 1 to 2 dilution factors lower than indolicidin for the gram-negative and gram-positive organisms tested (except P. acruginosa). In this example, indolicidin-DC had an approximately the same activity as indolicidin-C.

Example V

Microbial Killing by CP-11

Figure 3:
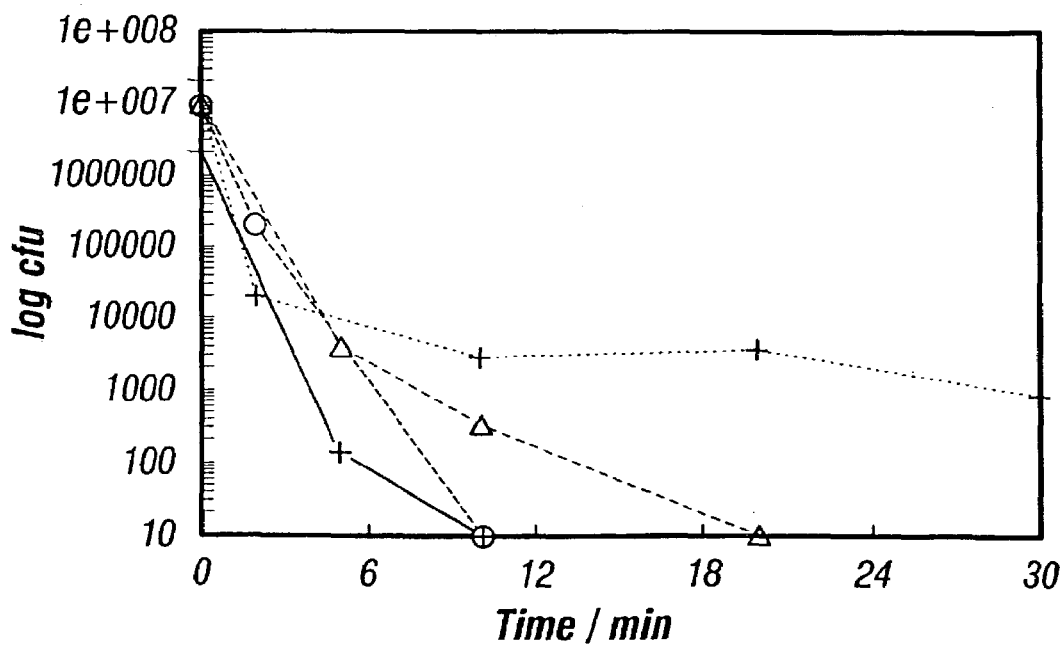
FIG. 3 shows a microbial killing curve for CP-11.

Killing curves were determined for CP-11 against E. coli, P. aeruginosa, S. aureus and C. albicans (FIG. 3). This assay was performed in 10 mM HEPES buffer, and viable counts were used to determine numbers of surviving cells. In all cases, CP-11 (at 32 µg/ml killed the test organisms rapidly. Within 30 minutes of adding the peptide, the viable count of gram-negative bacteria, gram-positive bacteria, and yeast decreased by at least 3 log orders. These data show that CP-11 is a potent antimicrobial peptide.

Example VI

Synergy Studies

In a variation of the MIC assay described above, the antimicrobial effects of the peptides were measured in the presence of antibiotics or other peptides. This assay showed that CP-11 and CP-13 were synergistic with polymyxin B, cefepime, ceftazidime. CP-11 was also synergistic with novobiocin and a cecropin/mellitin (CEME) hybrid peptide (Piers, supra). These experiments were performed by checkerboard titrations in which the synergizing peptide was diluted in two fold steps in one direction in a 96-well microtitre tray and antibiotics or peptides were diluted at right angles to the peptide. After addition of bacteria $10^4$-$10^5$ per well, and overnight incubation at 37° C., a fractional inhibitory concentration (FIC) was determined using an art known method (Le-Man, *Antibiotics in Laboratory Medicine,* 3rd ed., Williams and Wikins, pp 180-197, 1986). An FIC of 0.5 indicates synergism.

Example VIII

Binding of Antimicrobial Peptides to Purified Lipopolysaccharide

Peptides that bind lipopolysaccharide are thought to potentially function as anti-endotoxins. The binding of various CP peptides to P. aeruginosa H103 lipopolysaccharide (LPS) was measured in a dansyl polymyxin B (DPX) displacement assay as described by Moore et al. (AAC, 26 (1986) 496-500). Briefly, DPX exhibits enhanced fluorescence when it is bound to LPS. Purified LPS was saturated with DPX by titrating LPS with samples of DPX until maximum fluorescence was reached. Fluorescence was measured in a Perkin-Elmer 650-10S fluorescence spectrophotometer and displacement of DPX was measured as a decrease in fluorescence upon the addition of an antimicrobial peptide.

Table 4 shows the percentage of DPX fluorescence remaining bound to LPS as a function of peptide concentration. Each peptides $I_{50}$ value, which is the concentration at which 50% of the maximal DPX was displaced from the LPS, is shown. Also shown is the $I_{max}$ value, which represents the maximum displacement of LPS expressed as a percentage, where 100% indicates displacement of all bound DPX.

TABLE 4

Binding of antimicrobial peptides to purified lipopolysaccharide

| Peptide | $I_{50}$ of DPX displacement µM | $I_{max}$ % |
|---|---|---|
| Indolicidin | 8.5 | 62 |
| Indolicidin-C | 1.2 | 66 |
| CP-11 | 4.3 | 75 |
| CP-11C | 3.1 | 78 |

As is shown above, CP-11C were more effective in displacing DPX from P. aeruginosa LPS than the indolicidin. The relatively low $I_{50}$ concentration of the CP-11 and CP-11C reflects the relatively high affinity of these compounds for purified P. aeruginosa H103 LPS. The $I_{50}$ of $Mg^{2+}$ ions in these experiments was approximately 620 µM. These ions are the native divalent cations that normally bind LPS. Therefore, all of the tested peptides were capable of binding surface LPS by displacing such ions.

Example VIII

Membrane Permeabilization

Figure 4:
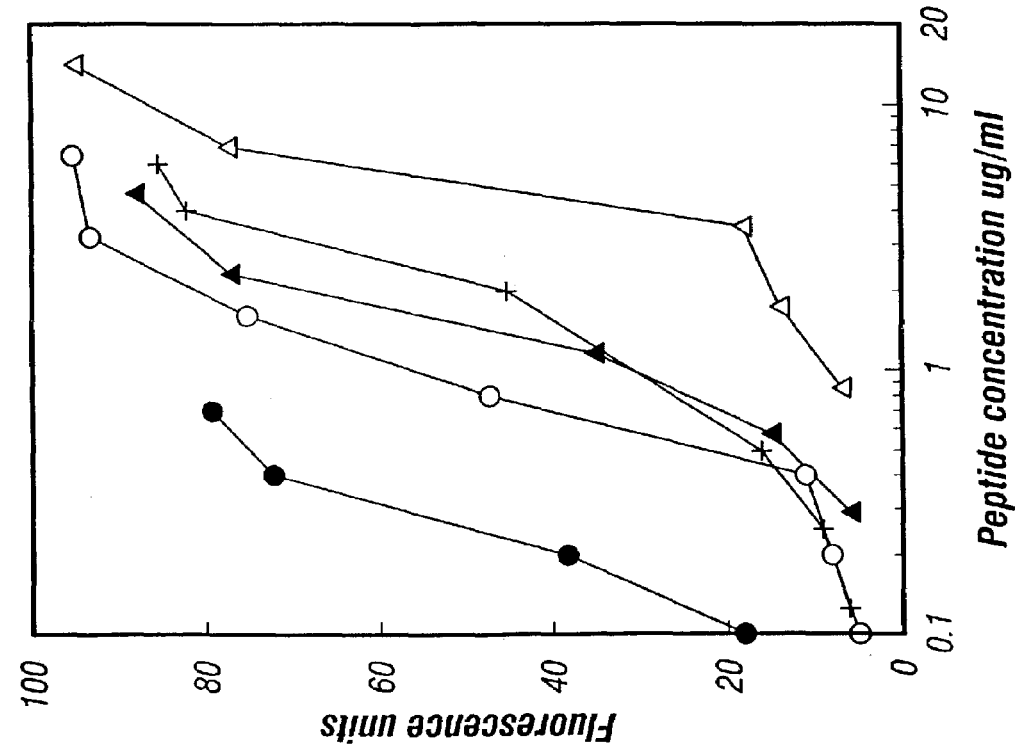
FIG. 4 shows the ability of antimicrobial peptides to permeabilize the outer membrane of bacteria. Polymyxin (solid circle), indolicidin (open triangle), indolicidin-C (cross), CP-11 (solid triangle). CP 11C (open circle).
Figure 7:
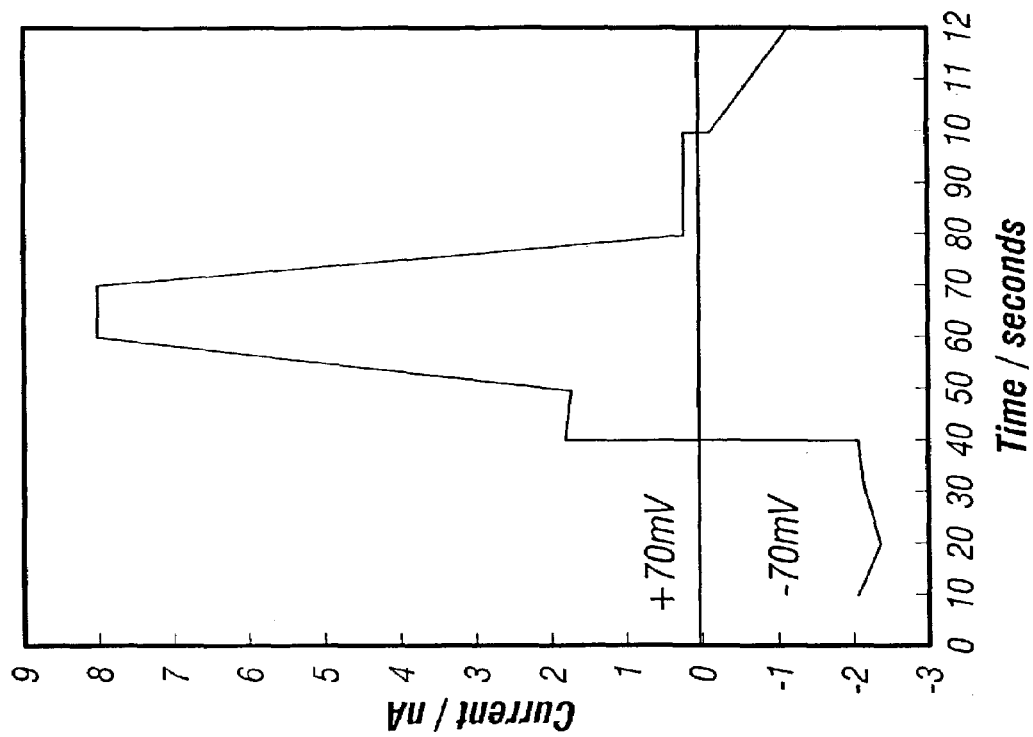
FIG. 7 shows the voltage sign dependence of indolicidin.

The degree of outer membrane permeabilization of E. coli UB1005 by the synthetic peptides was determined in a 1-N-phenylnapthylamine (NPN) uptake assay (Loh et al. AAC, 26 (1984) 2311-2316). Briefly, NPN is a small (200 kD), hydrophobic molecule that when partitioned into the bacterial outer membrane, exhibits an increase in fluorescence. Therefore, using a fluorescence spectrophotometer, an increase in fluorescence in the presence of a peptide indicates that the peptide can permeabilize the bacterial outer membrane. Fluorescence is measured as a function of the concentration of peptide, as shown in FIG. 4. This example shows that the permeabilization of E. coli to NPN, by CP-11C was greater than that by CP-11. Similarly, permeabilization by indolicidin-C was greater than that by indolicidin. In addition CP-11 was substantially better able to permeabilize the outer membrane of E. coli than was indolicidin.

Figure 5:
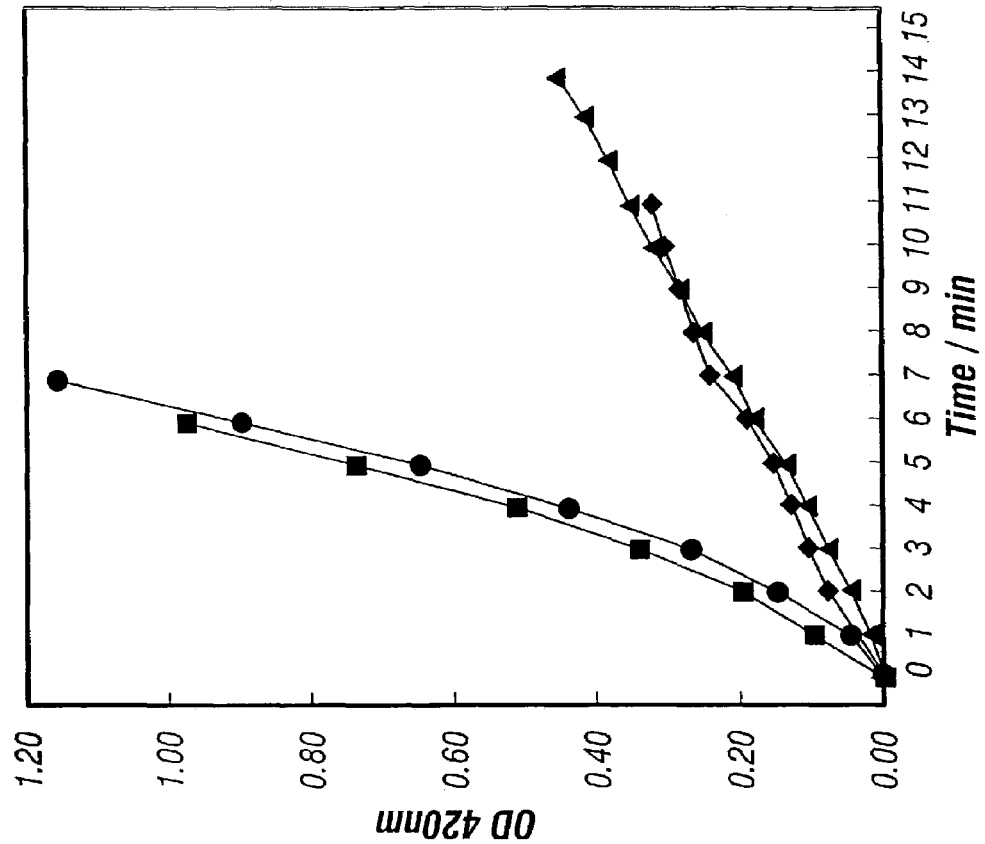
FIG. 5 shows the ability of antimicrobial peptides to permeabilize the inner membrane of bacteria. 16 µg/ml indolicidin (circle), 4 µg/ml indolicidin (triangle) 4 µg/ml CP-11 (square), 16 µg/ml indolicidin+CCP pre-treatment (diamond).

Permeabilization of the E. coli inner membrane was measured using E. coli ML-35, which is a lactose permease deficient strain that has constitutive cytoplasmic β-galactosidase activity (Lehrer et al., J. Clin. Invest. 84 (1989) 553-561). "Unmasking" of the β-galactosidase activity by due to permeabilizing of the inner membrane can be detected using the substrate ONPG (o-nitrophenyl-β-D-galactoside). Hydrolysis of ONPG can be followed spectrophotometrically at 420 nm. FIG. 5 shows that CP-11 permeabilize the inner membrane of *E. coli* at peptide concentrations that were 4 fold lower than the concentration of indolicidin required. Both of the peptides permeabilized the membrane after little or no lag time. These data show that, not only is the inner membrane the putative primary target for CP-11, but also the peptide reaches this target rapidly. Therefore, crossing of the outer membrane must also be a rapid process.

Example IX

Planar Lipid Bilayer Analysis

In order to gain insight into the mechanism by which these cationic peptides permeabilize the cytoplasmic membrane of bacteria, the effects of the peptide indolicidin on planar lipid bilayers were examined using the standard technique of black lipid bilayer analysis (Benz and Hancock, Biochim. Biophys. Acta 646 (1981) 298-308). Briefly, lipid bilayers (made from 1.5% (w/v) phosphatidylcholine and phosphotidylserine (5:1 in n-decane) were formed across a $0.2\ mm^2$ hole separating two compartments of a teflon chamber containing 1M KCl adjusted to pH 7.0 with $KH_2PO_4$. Calomel electrodes connected via a salt bridge (Metrohm) were placed in each compartment, one connected to a voltage source and the other connected to a Keithley-multimeter. The orientation of the voltage was designated with respect to the addition of the peptide to the cis-side with a trans-negative potential indicated by a minus sign. To detect single depolarization events, one electrode was connected to a current amplifier and chart recorder.

Figure 6:
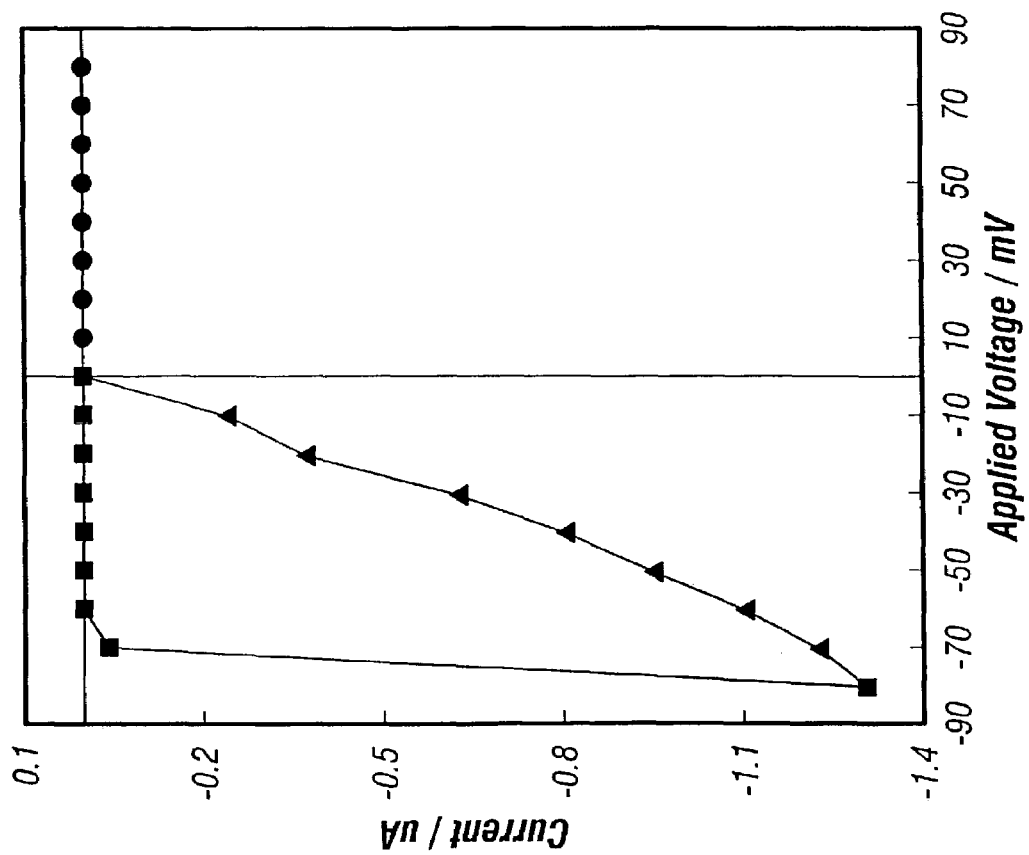
FIG. 6 shows the voltage/current relationship for indolicidin. Increasing potential, negative (square), positive (circle), decreasing negative potential (triangle).

The current-voltage characteristics of indolicidin characterized by macroscropic conductance experiments are shown in FIG. 6. The increase in voltage had only a minor effect on the current produced by permeabilization of the bilayer by indolicidin below −70 mV. At and above −70 mV, there was a dramatic increase in current. The requirement by indolicidin for a trans-membrane potential in excess of −70 mV makes the action of the peptide against the cytoplasmic membrane voltage-dependent. When the voltage was reduced from −80 mV back to 0 mV, the decrease was linear (FIG. 6). This indicates that the threshold potential may only be required to draw the peptide into the bilayer, and once this has occurred, the channels remain relatively stable. Growing bacteria have a trans-membrane potential in excess of −140 mV at neutral pH. The requirement of a negative potential of 70 mV for activity was confirmed by the reversal of the potential to +70 mV, resulting in a large reduction in activity (FIG. 6).

Figure 8:
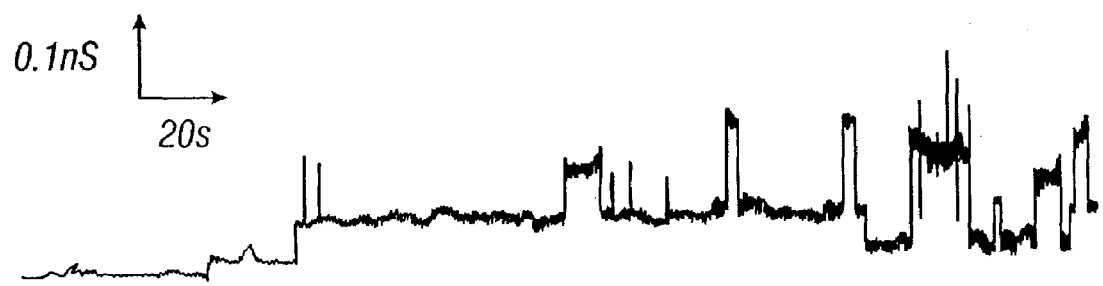
FIG. 8 shows single channel conductances produced by indolicidin in planar lipid bilayers.

The increase in membrane current caused by indolicidin was due, at least in part, to the formation of single channels (FIG. 8). Single channel conductances varied from 0.05-0.15 nS. However, channels of approximately 0.13 nS were repeatedly observed. CP-11 was also shown to form channels of similar dimensions.

Example X

In vivo Efficacy of Antimicrobial Peptides

The in vivo efficacy of CP-11 and CP-11CN was measured in a *P. aeruginosa* infection model of immunosuppressed mice (Cryz et al. 39:3 (1983) 1067-1071). Mice were rendered leukopenic by a series of three intraperitoneal (IP) injections of cyclophosphamide. CD-1 mice received cyclophosphamide on Days 0, 2, and 4 at 150 μg/g of mouse weight. On Day 4, the mice were challenged with 100 live *P. aeruginosa* M2 bacteria, and test groups received cationic peptide (8 mg/kg) in 100 μl $dH_2O$ at thirty minutes after injection of bacteria. In one experiment (summarized in Table 6), mice received an additional cationic peptide injection at 17 hours after bacterial challenge. The results of these experiments are summarized in Tables 5 and 6.

TABLE 5

Influence of a single dose of cationic peptide on survival of neutropenic mice challenged IP with *P. aeruginosa* strain M2

| Therapy | % Survival | | | | |
|---|---|---|---|---|---|
| | 17 hr | 24 hr | 41 hr | 48 hr | 65 hr |
| No peptide (n = 6) | 100 | 50 | 0 | 0 | 0 |
| CP-11CN (n = 6) | 100 | 66.7 | 33.3 | 33.3 | 16.7 |
| CP-11 | 100 | 100 | 33.3 | 22.2 | 11.1 |

TABLE 6

Influence of two doses of cationic peptide on survival of neutropenic mice challenged IP with *P. aeruginosa*

| Therapy | % Survival | | | | | |
|---|---|---|---|---|---|---|
| | 17 hr | 24 hr | 41 hr | 48 hr | 65 hr | 72 hr |
| No peptide (n = 7) | 100 | 86 | 14.3 | 0 | 0 | 0 |
| CP-11 (n = 8) | 100 | 100 | 37.5 | 25 | 25 | 25 |

This example shows that CP-11 and CP-11CN each inhibit the fatal effects of infection with *P. aeruginosa*. In addition, these data show that multiple doses of the antimicrobial peptide prolong survival.

Example XI

Effect of Peptides on Red Blood Cells

This example shows that CP-11, CP-11C, and CP-13 are less toxic to human cells than is indolicidin. Freshly collected human blood was mixed with heparin and centrifuged to remove the buffy coat. The resulting erythrocytes were washed three times in 0.85% saline and stored at 4° C. Serial dilutions of the peptides in saline were prepared in round bottomed microtitre plates using 100 μl volumes. Red blood cells were diluted with saline to 1/25 of the packed volume of cells and 50 μl of red blood cells were added to each well. Plates were incubated while rocking at 37° C., and the concentration of peptide required for red blood cell lysis of more than 80% of cells (i.e., visible lysis) was determined at 4 and 24 hours (Table 7).

TABLE 7

Lysis of red blood cells

| | Lowest concentration causing lysis μg/ml | |
|---|---|---|
| | 4 hours | 24 hours |
| Indolicidin | >128 | 32 |
| Indolicidin-C | 32 | 32 |

TABLE 7-continued

Lysis of red blood cells

| | Lowest concentration causing lysis μg/ml | |
|---|---|---|
| | 4 hours | 24 hours |
| CP-11 | >128 | >128 |
| CP-11C | >128 | 64 |
| CP-13 | >128 | 128 |

These data show that, while indolicidin is toxic to red blood cells at 32 μg/ml, but that CP-11, CP-11C, and CP-13 are significantly less toxic to red blood cells. Additional experiments have shown that CP-11 is also less toxic than indolicidin to T-lymphocytes (data not shown).

Example XII

Production of Additional Antimicrobial Peptides

The protein structure determinations made above have enabled the rational design of antimicrobial peptides, many of which exhibit increased antimicrobial activity and decreased toxicity. Expression and purification of various cationic peptides has previously been described (Hancock et al., U.S. Ser. No. 08/575,052, incorporated herein by reference, and Gene, 134 (1993) 7-13). In order to recombinantly express various antimicrobial peptides described below, oligonucleotides representing both strands of DNA encoding the various peptides were synthesized on an Applied Biosystems 392 DNA/RNA synthesizer using conventional methods. After annealing of the strands of DNA, the resulting DNA fragments were cloned into the *Staphyloccus aereus* expression vector pRIT5. Following transformation of the various clones into *E. Coli* DH5α, the recombinant plasmids were purified and sequenced and then electroporated (Bio Rad Gene Pulser Transfection Apparatus) into *S. aereus* K147. Nine peptides were expressed in this system, and their relative antimicrobial activities were determined by measuring the antimicrobial MICs of crude preparations of the cationic peptides against *Salmonella typhimurium* 14028S (Piers, et al., supra). Relative activities based on these measurements are presented in Table 8.

TABLE 8

Relative antimicrobial activity of recombinant peptides

| Peptide | Amino acid sequence | SEQ ID NO: | Gram-negative activity relative to indolicidin |
|---|---|---|---|
| Indolicidin-R | ILPWKWPWWPWRR | 16 | 1X |
| CP-1R | ILKPWKWPWWPWRR | 3 | 0.5X |
| CP-3R | ILPWKKWPWWRWRR | 4 | 4X |
| CP-4R | ILKKWPWWPWRR | 5 | 0.5X |
| CP-pM | ILPWKWPWRR | 10 | 0.2X |
| CP-pM1b | ILPWKWFFPPWPWRR | 21 | 0.2X |
| CP-pM2a | ILPWKWPWWPWWPWRR | 11 | 1.5X |
| CP-pM2b | ILPWKWPPWPPWPWRR | 22 | 1.5X |
| CP-pM5 | ILPWKWPWWPWWKKPWRR | 12 | 0.5X |

Methods used to express and purify cationic and microbial peptides as protein A fusion proteins have been described (Piers et al., Gene, 134 (1993) 7-13). Here, culture supernatants of cells containing pRIT5 expressing various antimicrobial peptides were passed over an IgG SEPHAROSE™ column, according to conventional protocols. The expressed protein then was eluted in 0.5 M acetic acid to give a relatively pure sample. Following lyophilization, the sample was resuspended in 70% formic acid containing 1M cyanogen bromide. Digestion was performed overnight under nitrogen in light sealed tubes. The reaction was stopped by a ten fold dilution in sterile distilled water, and the sample was lyophilized. The peptide was further purified by passing the sample over a BIO-GEL® P100 gel sieving column, and fractions were analyzed by UV absorbance at 280 nm and acid-urea Page. All fractions containing pure peptide were pooled and lyophilized. The peptides were resuspended in sterile distilled water and stored at –80° C.

In a MIC assay, the peptides CP-3R, CP-pM2a and CP-pM2b had increased activity against gram-negative bacteria when compared with indolicidin-R (i.e., Recombinant indolicidin). The remaining peptides had the same or decreased activity when compared with indolicidin-R. Indolicidin-R and CP-3R subsequently were purified, and the MIC data is summarized in Table 9. CP-3R had increased activity against *E. coli, P. aeruginosa,* and *S. typhimurium.*

TABLE 9

MIC values for recombinant peptides

| Organism | Indolicidin-R | CP-3R |
|---|---|---|
| *E.coli* UB1005 | 32 | 8 |
| *P. aeruginosa* K799 | >32 | 8 |
| *S. typhimurium* 14028S | 16 | 8 |
| *S. aureus* RN4220 | 16 | 8 |
| *S. epidermidis* C621 | 16 | 4 |
| *C. albicans* C627 | >32 | >32(8) |

*Partial killing was observed in dilutions down to 8 μg/ml

Example XIII

Peptide Design

Based upon the structure and function analysis of antimicrobial cationic peptides summarized above, Applicants have devised a formula that can be used to produce additional cationic peptides. Peptides having an amino acid sequence encompassed by one of the formulas shown below (shown using the one-letter amino acid code; SEQ ID NO: 23-26) are expected to have antimicrobial activity.

$X_1X_1PX_2X_3X_2P(X_2X_2P)_nX_2X_3(X_5)_o$;  (SEQ ID NO:23)

$X_1X_1PX_2X_3X_4(X_5)_rPX_2X_3X_3$;  (SEQ ID NO:24)

$X_1X_1X_3(PW)_uX_3X_2X_5X_2X_2X_5X_2(X_5)_o$; and  (SEQ ID NO:25)

$X_1X_1X_3X_3X_2P(X_2X_2P)_nX_2(X_5)_m$;  (SEQ ID NO:26)

wherein:
 m is 1 to 5;
 n is 1 or 2;
 o is 2 to 5;
 r is 0 to 8;
 u is 0 or 1;
 $X_1$ is Isoleucine, Leucine, Valine, Phenylalanine, Tyrosine, Tryptophan or Methionine;
 $X_2$ represents Tryptophan or Phenylalanine;
 $X_3$ represents Arginine or Lysine;
 $X_4$ represents Tryptophan or Lysine; and X$_5$ represents Phenylalanine, Tryptophan, Arginine, Lysine, or Proline.

In accordance with the formula provided above, Applicants have designed a series of cationic peptides expected to have antimicrobial activity. These peptides are listed in Table 10. This list is not exhaustive of the antimicrobial peptides of the invention. Those skilled in the art will recognize that, following the above formula, additional antimicrobial cationic peptides can readily be synthesized. If desired, the antimicrobial activity of such peptides can be measured in conventional assays (e.g., MIC assays). Because Applicants have identified the structural components necessary for antimicrobial activity, it is expected that essentially all of the peptides encompassed by the formula will have antimicrobial activity. It is not necessary that these peptides have activity equivalent to, or better than, the peptides exemplified herein, provided that the peptide has a detectable level of activity (e.g., in a MIC assay).

TABLE 10

| CP-14 | ILKKWPWWPWKRR | (SEQ ID NO: 17) |
|---|---|---|
| CP-15 | ILKKWPWWRWRR | (SEQ ID NO: 27) |
| CP-17 | ILKKFPFFPFKKK | (SEQ ID NO: 29) |
| CP-18 | ILKKWAWWPWRRK | (SEQ ID NO: 30) |
| CP-19 | ILKKWPWWAWRRK | (SEQ ID NO: 31) |
| CP-20 | ILKKWPWWPWKKK | (SEQ ID NO: 32) |
| CP-21 | ILRRWPWWPWRRR | (SEQ ID NO: 33) |
| CP-22 | WWKKWPWWPWRRK | (SEQ ID NO: 34) |
| CP-23 | FFKKWPWWPWRRK | (SEQ ID NO: 35) |
| CP-25 | FFKKFPFFPFKKK | (SEQ ID NO: 36) |
| CP-26 | ILKKWPWWPWWPWRRK | (SEQ ID NO: 38) |
| CP-27 | ILKKWPWWPWRWWRR | (SEQ ID NO: 39) |
| CP-28 | ILKKWPWWPWRRWWK | (SEQ ID NO: 40) |
| CP-29 | ILKKWPWWPWPPRRK | (SEQ ID NO: 41) |
| CP-30 | ILKKWPWWPWPPFFRRK | (SEQ ID NO: 42) |

Example XIV

Synthesis and Expression of a Library Encoding Peptide Variants

A library of peptide variants was created in *S. aureus* using the expression vector pRIT5. DNA strands of a combinatorial library of DNAs encoding indolicidin variants were synthesized on the Applied Biosystems Canada Incorporated (Ontario, Canada) 392 DNA/RNA synthesizer. These oligonucleotides were constructed in 3 sections. The first section, the 3' end containing restriction endonuclease sites and stop sequences, was synthesized using standard protocols (Applied Biosystems Canada Inc.). The second section, encoding the indolicidin peptide sequence, was synthesized using nucleotide stocks that were doped with each of the other three nucleotides. The relationship between the doping concentration and the mutation rate is defined by an equation described by McNeil and Smith (Mol. Cell. Biol., 5 (1985) 3545-3551). The third section also was synthesized according to standard protocols (Applied Biosystems Canada Inc.). The resulting oligonucleotides contained a pool of randomly mutated indolicidin sequences flanked by conserved 3' and 5' sequences. The oligonucleotide pool was then made double stranded by PCR using primers designed to hybridize to the 3' and 5' sequences. The PCR reaction was performed in 100 μl using the conditions and parameters shown below.

PCR Reaction Parameters
  1 minute 94° C., 1 minute 50° C., 1 minute 72° C.
  Cycle repeated 30 times

| PCR reaction conditions | |
|---|---|
| | Final concentration |
| 10X PCR reaction buffer | 1X |
| 10X dNTPs | 1X |
| Taq polymerase | 1 unit |
| Primer 1 (GCATATCGAATTCCATG) | 40 ng (SEQ ID NO: 43) |
| Primer 2 (CTGCAGGTCGACGAGC) | 40 ng (SEQ ID NO: 44) |
| MgCl$_2$ | 10 mM |
| DNA Template | 100 ng |

The amplified product was digested at restriction endonuclease sites located in the conserved flanking regions of the DNA fragment, and the product was agarose gel purified using the Mermaid Glassfog (BIO 101, La Jolla, Calif. US) DNA purification kit. After cloning the DNA fragments into pRIT5, the randomly mutated pool of recombinant plasmids was electroporated into *S. aureus* K147, and the clones were stored as a library at −80° C. Screening of a number of recombinant *S. aureus* strains showed that 75% of the recombinant strains expressed the protein A/peptide fusion product. Sequencing of a random selection of clones revealed 4 to 8 base pair changes that resulted in 4 to 6 amino acid substitutions (see below).

```
Indolicidin   ILPWKWPWWPWRR    (SEQ ID NO: 16)

Variant 1     ILPWICPWRPSKAN   (SEQ ID NO: 13)

Variant 2     IVPWKWTLWPWRR    (SEQ ID NO: 14)

Variant 3     TLPCLWPWWPWSI    (SEQ ID NO: 15)
```

This method can be used to produce a recombinant peptide library expressing peptides with a predetermined mutation rate.

Example XV

Screening of the Recombinant Peptide Library

A screening protocol was developed to detect an increase in antibacterial activity in clones expressing random variants of the peptides produced as described above. This protocol allows one to screen large numbers of recombinant clones.

In this method, 100 ml LB high salt broth (containing 10 g/ml chloramphenicol) was inoculated with 1 ml of an overnight culture of a candidate clone. The culture was grown to OD$_{600}$ at 37° C. while shaking at 180 rpm. Following centrifugation at 2,500 rpm for 10 minutes, the supernatant was removed and passed over a 1 ml IgG SEPHAROSE™ column (Pharmacia). The fusion protein was eluted from the column with 0.5 M acetic acid (pH 3.0), and the second 1 ml aliquot contained virtually all of the fusion protein.

The 1 ml aliquot was then lyophilized and resuspended in 75 μl 70% formic acid containing 1M cyanogen bromide. The reaction was light sealed under nitrogen in a 1.5 ml screw top tube and rotated overnight. Following a ten fold dilution in sterile distilled water, the reaction was again lyophilized, washed in 200 μl sterile distilled water, re-lyophilized, and resuspended in 100 μl no salt LB broth.

The peptide preparation was used in a modified broth MIC assay using a 96 well microtiter plate. A 100 μl aliquot of LB no salt broth was placed into each well. The 100 μl peptide preparation was added to the first well, and a doubling dilution series performed through 8 wells. An inoculum of $10^2$ to $10^3$ *Salmonella typhimurium* 14028S (a defensin supersusceptible mutant) was added to each well, and the plate was incubated overnight at 37° C.

The microtiter plate was examined after 24 hours. The extract from *S. aureus* strain K148 (Piers et al., supra) that contained pRIT5 and lacked an indolicidin insert exhibited no antibacterial activity. However, strains expressing indolicidin-R and CP-R3 prevented growth of the test organism in the first, and first and second, wells, respectively. Therefore, peptides capable of killing at dilutions higher than 0.5 can be identified as having an increased antimicrobial activity relative to the reference protein. This method also can be used to identify peptides having antimicrobial activity that is equivalent to, or less than, the reference protein.

Example XVI

Induction of TNF in RAW 264.7 Macrophage Cells

The physiological mechanism(s) by which endotoxin exerts its effect on humans involves the release of inflammatory cytokines, particularly tumor necrosis factor (TNF). CP-11 was tested for its ability to block the induction of TNF by binding LPS. This was tested in vitro in a murine RAW 264.7 macrophage cell line and in vivo for ability to reverse death in a murine endotoxic shock model and in a *P. aeruginosa* infection model.

The effect of CP-11 and indolicidin on LPS-induced TNF in macrophages was examined using the murine RAW 264.7 macrophage cell line, which produces TNF in response to LPS. The cell line was grown by seeding $10^6$ cells into a 162 $cm^2$ cell culture flask, which was incubated at 37° C. in 5% $CO_2$ for 1 week. RAW cell media [Dulbecco's Modified Eagle Medium with Hepes buffer 450 ml (2.4 mM); L-glutamine 3 ml (400 mM); Pen/Strep 3 ml ($10^4$ U/ml of Pen, 1 mg/ml strep); and 10% heat inactivated fetal bovine serum (FBS) 50 ml] was then removed from the cell culture flasks. A 10 ml aliquot of solution was added to each flask and incubated at 37° C. for 10 minutes. The cells were removed from the flasks, diluted in RAW cell media, and centrifuged for 6 minutes. The cell pellet was resuspended in 5 ml of media/flask. A 100 µl cell suspension was removed and added to 400 µl of trypan blue, and the cells were counted using a hemocytometer. The cell suspension was diluted to $1 \times 10^6$ cells/ml and 1 ml of suspension was added per well of a 24 well plate. The 24 well plates were incubated at 37° C. in 5% $CO_2$ overnight for use in the assay.

After an overnight incubation, the media was aspirated from all the wells. LPS was added at 100 ng/100 µl. Peptide was added at the desired concentration/100 µl to specified wells. RAW cell media was added to all the wells so they had a final volume of 1 ml. The plates were then incubated for six hours at 37° C. in 5% $CO_2$. The supernatant was then removed from the wells and stored overnight at 4° C.

Experiments were also performed using whole bacteria in a transwell filter system. Viable Bort *E. coli* and *P. aeruginosa* were incubated in 0.22 µm filter inserts, which prevented direct contact of the bacteria with the macrophage cells yet allowed products released by the bacteria (e.g., LPS) to interact with the cells. Overnight cultures were diluted in phosphate buffered saline to an $OD_{600}$ of 0.3 (approximately $10^8$ cells/ml). The bacteria were further diluted 1:100 and counted.

The supernatants from the above tissue culture experiments were used in the cell cytotoxic L929 assay. The RAW cell supernatants were diluted in a three fold dilution series in 96 well plates. A 50 µl aliquot of TNF media was added to all of the wells in all of the plates except to those wells in the first row. Ten µl of murine TNF standard (20 ng/ml) and 90 µl of TNF media were added in duplicate to the plate and diluted 1:2 down the plate to the second to last row.

TNF-sensitive L929 mouse fibroblast cells were seeded at $10^6$ cells/$162 cm^2$ cell culture flask and left to grow for 1 week. L929 cells were removed from the flask with 10 mls of trypsin EDTA/flask and incubated 3-5 minutes. The cell suspension was diluted, and then centrifuged for 6 minutes. The pellet was resuspended in 5 mls of fresh L929 media/flask and counted (same as RAW cells). Cell suspension was diluted to $10^6$ cells/ml. One hundred µl was used to inoculate each well of the 96 well plates with the supernatants. (L929 Growth Media was the same as RAW cell media except, instead of FBS, 50 mls of 10% heat inactivated horse serum was utilized; TNF Assay Media was the same as RAW cell media except 4 µg/ml Actinomycin D.) The plates were incubated for two days at 37° C., 5% $CO_2$. The plates were then read at 570 nm in a ELISA plate reader with 690 nm reference filter. One unit of TNF activity was defined as the amount required to kill 50% of the L929 cells. The TNF level in Units per ml therefore was the reciprocal of the dilution that led to a 50% killing of L929 cells. Computations were performed using the ELISA+ program.

Figure 9:
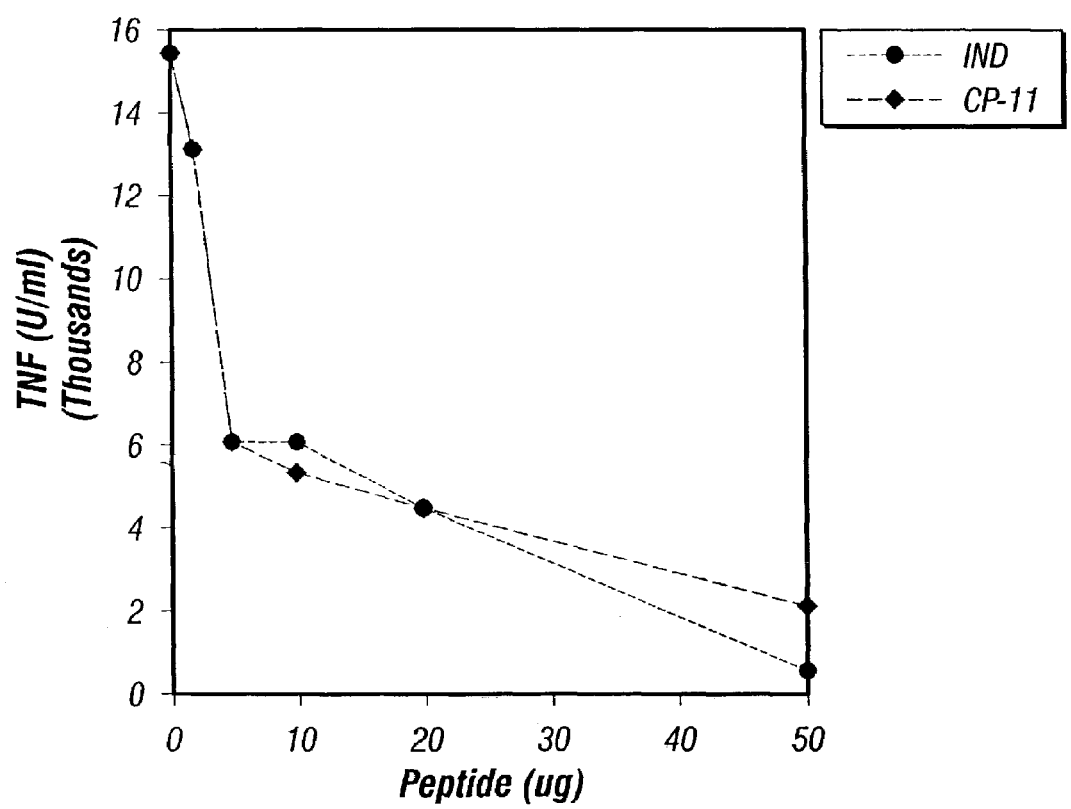
FIG. 9 shows the effects of peptides on *E. coli* 0111:B4 LPS-induced TNF.
Figure 10:
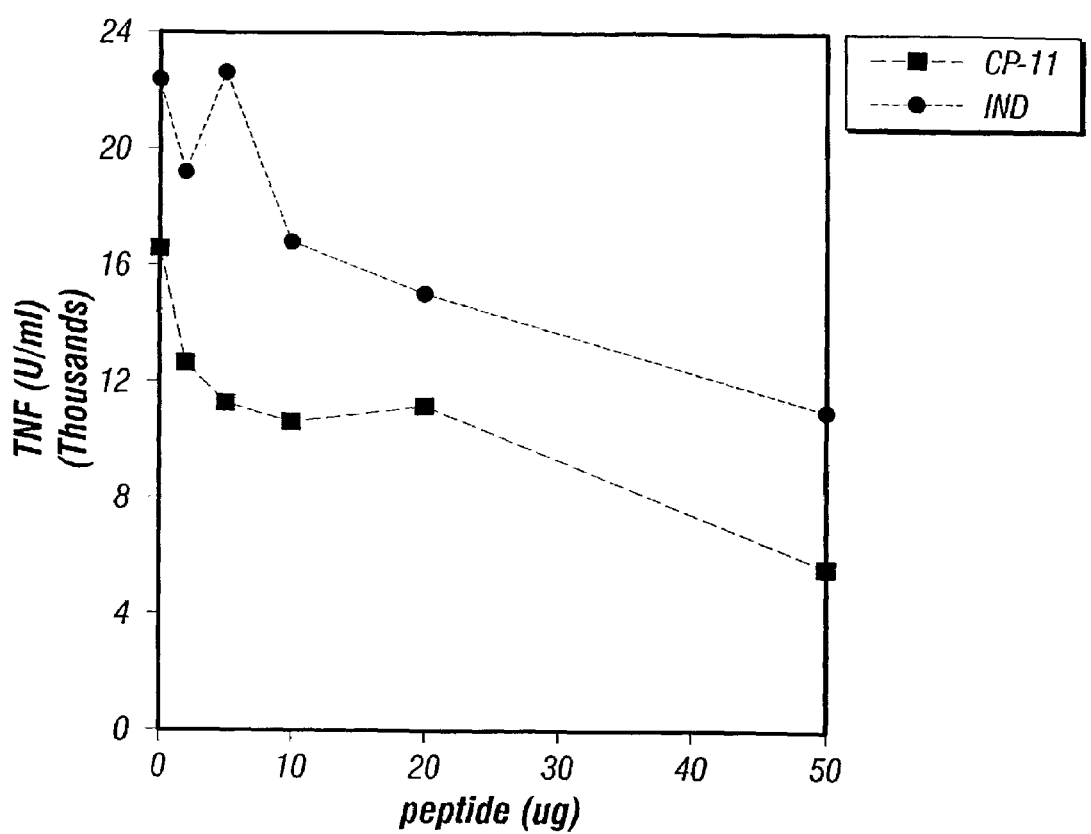
FIG. 10 shows the effect of peptides on *P. aeruginosa* LPS-induced TNF.

FIG. 9 shows levels of TNF (U/ml) produced by the macrophage cells after a 6 hour treatment with increasing amounts (0, 2, 5, 10, 20, or 50 µg) of either CP-11 or indolicidin peptide and 100 ng of *E. coli* 0111:B4 LPS. The data indicates that both peptides efficiently reduced the level of LPS-induced in macrophages by LPS by 70% and 71% respectively. The results of a 6 hour incubation with *P. aeruginosa* LPS and indolicidin or CP-11 are shown in FIG. 10. Fifty µg of CP-11 and indolicidin decreased the TNF production by 51% and 67% respectively. Fifty µg of indolicidin and PP-11 decreased TNF production by macrophages incubated with 100 ng Bort *E. coli* LPS by 68% and 74% respectively.

Figure 11:
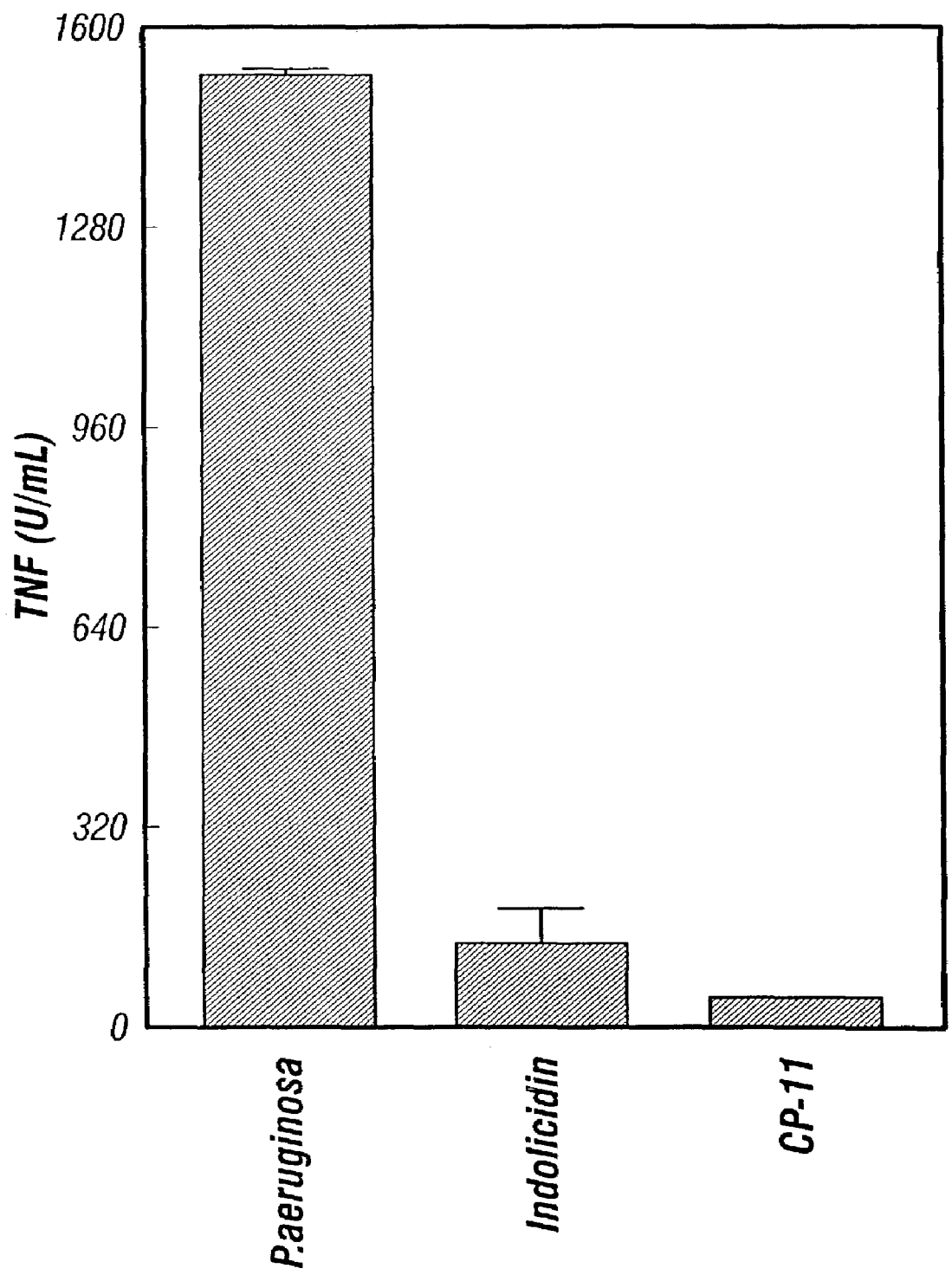
FIG. 11 shows the effect of cationic peptides on LPS released by *P. aeruginosa*.
Figure 12:
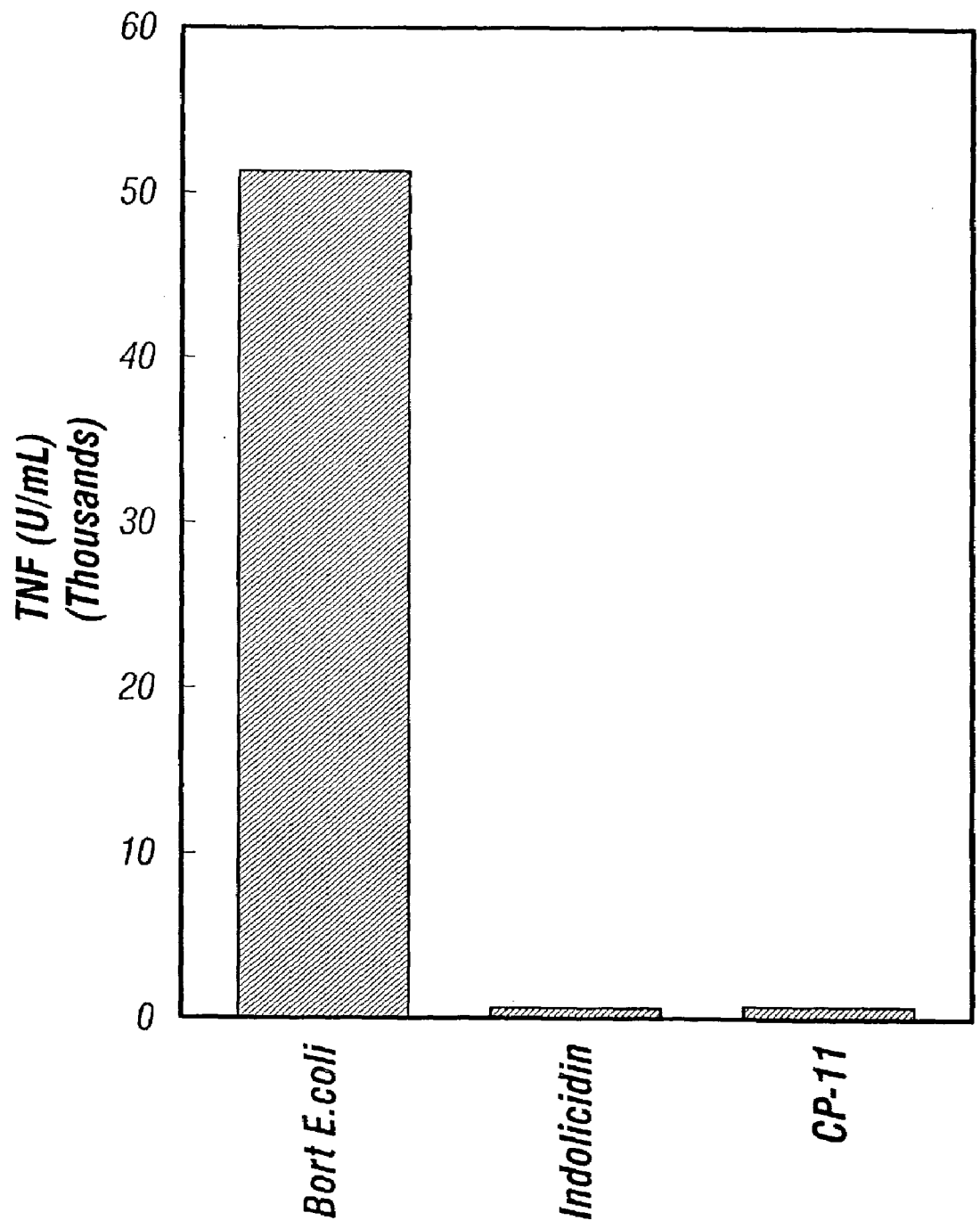
FIG. 12 shows the effect of cationic peptides on LPS released by Bort *E. coli*.

In the experiments using intact bacteria, the peptides were able to effectively reduce the induction of TNF by the diffusible products of *P. aeruginosa* and *E. coli*. CP-11 and Indolicidin reduced the TNF-induction by LPS released by *P. aeruginosa* by 97% and 91% respectively (FIG. 11). Both peptides reduced the TNF-induction by Bort *E. coli* by 99% (FIG. 12).

To confirm that indolicidin was acting on LPS rather than directly upon macrophage cell lines, 20 µg of indolicidin was added to RAW cells and incubated for 60 minutes prior to aspiration of the medium and washing the cells 3 times with HBSS (Hanks Buffered Salt Solution). Addition of 100 ng of LPS to the washed RAW cells resulted in a high level of TNF induction (4168 Units of TNF per ml), suggesting that the indolicidin had not permanently depressed the ability of RAW cells to induce TNF in response to LPS addition. In contrast, the aspirated medium containing indolicidin could depress the ability of fresh RAW cells to induce TNF in response to 100 ng of *E. coli* Bort LPS by 74%. Up to 50 µg of CP-11 or indolicidin caused no apparent decrease in Raw cell viability as judged by Trypan blue exclusion.

Example XVII

Murine Endotoxic Shock Model

The ability of indolicidin and variants to protect against LPS-induced endotoxemia was assessed in vivo. Mice (8-10 weeks old) were injected intraperitoneally (IP) with 20 mg D-galactosamine (Dgal) to sensitize them to LPS according to the model of Galanos (Galanos, C., M. A., Freudenberg and W. Reutter, 1979, Galactosamine sensitization to the lethal effects of endotoxin. Proc. Natl. Acad. Sci. USA 76:5939), followed by 200 μg peptide in 100 μl. Immediately afterwards LPS (10 μg) in 100 μl was injected. The mice were observed 24 hours after injections and survivors noted. Injection of 200 μg of indolicidin-D, CP-11, or CP-11, or CP-11D did not cause mortality. When Dgal and LPS were also injected, that 200 μg of indolicidin reduced mortality reduced at 24 hours from 100% in controls to 60%. This example thus demonstrates that the cationic peptides of the invention have anti-endotoxin activity in vivo.

Although the invention has been described with reference to the presently preferred embodiment, it should be understood that various modifications can be made without departing from the spirit of the invention. Accordingly, the invention is limited only by the following claims.

What is claimed is:

1. A method of inhibiting the growth of a Gram positive bacterium, a Gram negative bacterium, or a yeast comprising contacting the bacterium or the yeast with an inhibiting effective amount of an isolated peptide selected from the group consisting of:

```
ILKKWPWWPWRRK          (SEQ ID NO:1);

ILKPWKWPWWPWRRKK       (SEQ ID NO:2);

ILKPWKWPWWPWRR         (SEQ ID NO:3);

ILPWKKWPWWRWRR         (SEQ ID NO:4);

ILKKWPWWPWRR           (SEQ ID NO:5);

ILPWKWPWWPWRKWR        (SEQ ID NO:6);

ILPWKWPWWPWRRWR        (SEQ ID NO:7);

ILPWKWPWRR             (SEQ ID NO:10);

ILPWKWPWWPWWPWRR       (SEQ ID NO:11);

ILPWKWPWWPWWKKPWRR     (SEQ ID NO:12);

ILKKWPWWPWKWKK         (SEQ ID NO:18);

IKWPWYVWL              (SEQ ID NO:20);

ILPWKWFFPPWPWRR        (SEQ ID NO:21);

ILPWKWPPWPPWPWRR       (SEQ ID NO:22);

ILKKFPFFPPRRK          (SEQ ID NO:28); and

FFKKFPFFPFRRK          (SEQ ID NO:36).
```

2. The method of claim 1, wherein the method inhibits the growth of the Gram positive bacterium.

3. The method of claim 2, wherein the Gram positive bacterium is *Staphylococcus aureus* or *Staphylococcus epidermidis*.

4. The method of claim 1, wherein the method inhibits the growth of the Gram negative bacterium.

5. The method of claim 4, wherein the Gram negative bacterium is selected from the group consisting of *E. coli, P. aeruginosa*, and *S. typhimurium*.

6. The method of claim 1, further comprising contacting the bacterium or the yeast with at least one antibiotic.

7. The method of claim 6, wherein the antibiotic is selected from the group consisting of a β-lactam, novobiocin, and polymyxin B.

8. The method of claim 1, wherein the yeast is *Candida albicans*.

9. The method of claim 1, wherein the isolated peptide is C-terminally amidated or C-terminally methyl-esterified.

10. The method of claim 1, wherein the N-terminal amino acid of said SEQ ID NO: 1 is synthesized in D-form.

* * * * *

```
                           SEQUENCE LISTING

<160> NUMBER OF SEQ ID NOS: 44

<210> SEQ ID NO 1
<211> LENGTH: 13
<212> TYPE: PRT
<213> ORGANISM: Artificial sequence
<220> FEATURE:
<223> OTHER INFORMATION: SYNTHETIC PEPTIDE

<400> SEQUENCE: 1

Ile Leu Lys Lys Trp Pro Trp Trp Pro Trp Arg Arg Lys
1               5                   10

<210> SEQ ID NO 2
<211> LENGTH: 16
<212> TYPE: PRT
<213> ORGANISM: Artificial sequence
<220> FEATURE:
<223> OTHER INFORMATION: SYNTHETIC PEPTIDE

<400> SEQUENCE: 2

Ile Leu Lys Pro Trp Lys Trp Pro Trp Trp Pro Trp Arg Arg Lys Lys
1               5                   10                  15

<210> SEQ ID NO 3
<211> LENGTH: 14
<212> TYPE: PRT
<213> ORGANISM: Artificial sequence
<220> FEATURE:
<223> OTHER INFORMATION: SYNTHETIC PEPTIDE

<400> SEQUENCE: 3

Ile Leu Lys Pro Trp Lys Trp Pro Trp Trp Pro Trp Arg Arg
1               5                   10

<210> SEQ ID NO 4
<211> LENGTH: 14
<212> TYPE: PRT
<213> ORGANISM: Artificial sequence
<220> FEATURE:
<223> OTHER INFORMATION: SYNTHETIC PEPTIDE

<400> SEQUENCE: 4

Ile Leu Pro Trp Lys Lys Trp Pro Trp Trp Arg Trp Arg Arg
1               5                   10

<210> SEQ ID NO 5
<211> LENGTH: 12
<212> TYPE: PRT
<213> ORGANISM: Artificial sequence
<220> FEATURE:
<223> OTHER INFORMATION: SYNTHETIC PEPTIDE
```

```
<400> SEQUENCE: 5

Ile Leu Lys Lys Trp Pro Trp Trp Pro Trp Arg Arg
1               5                   10

<210> SEQ ID NO 6
<211> LENGTH: 15
<212> TYPE: PRT
<213> ORGANISM: Artificial sequence
<220> FEATURE:
<223> OTHER INFORMATION: SYNTHETIC PEPTIDE

<400> SEQUENCE: 6

Ile Leu Pro Trp Lys Trp Pro Trp Trp Pro Trp Arg Lys Trp Arg
1               5                   10                  15

<210> SEQ ID NO 7
<211> LENGTH: 15
<212> TYPE: PRT
<213> ORGANISM: Artificial sequence
<220> FEATURE:
<223> OTHER INFORMATION: SYNTHETIC PEPTIDE

<400> SEQUENCE: 7

Ile Leu Pro Trp Lys Trp Pro Trp Trp Pro Trp Arg Arg Trp Arg
1               5                   10                  15

<210> SEQ ID NO 8
<211> LENGTH: 15
<212> TYPE: PRT
<213> ORGANISM: Artificial sequence
<220> FEATURE:
<223> OTHER INFORMATION: SYNTHETIC PEPTIDE

<400> SEQUENCE: 8

Ile Leu Pro Trp Lys Trp Pro Trp Trp Pro Trp Lys Lys Trp Lys
1               5                   10                  15

<210> SEQ ID NO 9
<211> LENGTH: 11
<212> TYPE: PRT
<213> ORGANISM: Artificial sequence
<220> FEATURE:
<223> OTHER INFORMATION: SYNTHETIC PEPTIDE

<400> SEQUENCE: 9

Pro Trp Lys Trp Pro Trp Trp Pro Trp Arg Arg
1               5                   10

<210> SEQ ID NO 10
<211> LENGTH: 10
<212> TYPE: PRT
<213> ORGANISM: Artificial sequence
<220> FEATURE:
<223> OTHER INFORMATION: SYNTHETIC PEPTIDE

<400> SEQUENCE: 10

Ile Leu Pro Trp Lys Trp Pro Trp Arg Arg
1               5                   10

<210> SEQ ID NO 11
<211> LENGTH: 16
<212> TYPE: PRT
<213> ORGANISM: Artificial sequence
<220> FEATURE:
<223> OTHER INFORMATION: SYNTHETIC PEPTIDE
```

```
<400> SEQUENCE: 11

Ile Leu Pro Trp Lys Trp Pro Trp Trp Pro Trp Pro Trp Arg Arg
1               5                   10                  15

<210> SEQ ID NO 12
<211> LENGTH: 18
<212> TYPE: PRT
<213> ORGANISM: Artificial sequence
<220> FEATURE:
<223> OTHER INFORMATION: SYNTHETIC PEPTIDE

<400> SEQUENCE: 12

Ile Leu Pro Trp Lys Trp Pro Trp Trp Pro Trp Trp Lys Lys Pro Trp
1               5                   10                  15

Arg Arg

<210> SEQ ID NO 13
<211> LENGTH: 14
<212> TYPE: PRT
<213> ORGANISM: Artificial sequence
<220> FEATURE:
<223> OTHER INFORMATION: SYNTHETIC PEPTIDE

<400> SEQUENCE: 13

Ile Leu Pro Trp Ile Cys Pro Trp Arg Pro Ser Lys Ala Asn
1               5                   10

<210> SEQ ID NO 14
<211> LENGTH: 13
<212> TYPE: PRT
<213> ORGANISM: Artificial sequence
<220> FEATURE:
<223> OTHER INFORMATION: SYNTHETIC PEPTIDE

<400> SEQUENCE: 14

Ile Val Pro Trp Lys Trp Thr Leu Trp Pro Trp Arg Arg
1               5                   10

<210> SEQ ID NO 15
<211> LENGTH: 13
<212> TYPE: PRT
<213> ORGANISM: Artificial sequence
<220> FEATURE:
<223> OTHER INFORMATION: SYNTHETIC PEPTIDE

<400> SEQUENCE: 15

Thr Leu Pro Cys Leu Trp Pro Trp Trp Pro Trp Ser Ile
1               5                   10

<210> SEQ ID NO 16
<211> LENGTH: 13
<212> TYPE: PRT
<213> ORGANISM: Artificial sequence
<220> FEATURE:
<223> OTHER INFORMATION: SYNTHETIC PEPTIDE

<400> SEQUENCE: 16

Ile Leu Pro Trp Lys Trp Pro Trp Trp Pro Trp Arg Arg
1               5                   10

<210> SEQ ID NO 17
<211> LENGTH: 13
<212> TYPE: PRT
<213> ORGANISM: Artificial sequence
<220> FEATURE:
<223> OTHER INFORMATION: SYNTHETIC PEPTIDE
```

```
<400> SEQUENCE: 17

Ile Leu Lys Lys Trp Pro Trp Trp Pro Trp Lys Arg Arg
1               5                   10

<210> SEQ ID NO 18
<211> LENGTH: 14
<212> TYPE: PRT
<213> ORGANISM: Artificial sequence
<220> FEATURE:
<223> OTHER INFORMATION: SYNTHETIC PEPTIDE

<400> SEQUENCE: 18

Ile Leu Lys Lys Trp Pro Trp Trp Pro Trp Lys Trp Lys Lys
1               5                   10

<210> SEQ ID NO 19
<211> LENGTH: 12
<212> TYPE: PRT
<213> ORGANISM: Artificial sequence
<220> FEATURE:
<223> OTHER INFORMATION: SYNTHETIC PEPTIDE

<400> SEQUENCE: 19

Ile Leu Pro Trp Lys Trp Pro Trp Tyr Val Arg Arg
1               5                   10

<210> SEQ ID NO 20
<211> LENGTH: 9
<212> TYPE: PRT
<213> ORGANISM: Artificial sequence
<220> FEATURE:
<223> OTHER INFORMATION: SYNTHETIC PEPTIDE

<400> SEQUENCE: 20

Ile Lys Trp Pro Trp Tyr Val Trp Leu
1               5

<210> SEQ ID NO 21
<211> LENGTH: 15
<212> TYPE: PRT
<213> ORGANISM: Artificial sequence
<220> FEATURE:
<223> OTHER INFORMATION: SYNTHETIC PEPTIDE

<400> SEQUENCE: 21

Ile Leu Pro Trp Lys Trp Phe Phe Pro Pro Trp Pro Trp Arg Arg
1               5                   10                  15

<210> SEQ ID NO 22
<211> LENGTH: 16
<212> TYPE: PRT
<213> ORGANISM: Artificial sequence
<220> FEATURE:
<223> OTHER INFORMATION: SYNTHETIC PEPTIDE

<400> SEQUENCE: 22

Ile Leu Pro Trp Lys Trp Pro Pro Trp Pro Pro Trp Pro Trp Arg Arg
1               5                   10                  15

<210> SEQ ID NO 23
<211> LENGTH: 20
<212> TYPE: PRT
<213> ORGANISM: Artificial sequence
<220> FEATURE:
<223> OTHER INFORMATION: SYNTHETIC PEPTIDE
```

```
<220> FEATURE:
<221> NAME/KEY: VARIANT
<222> LOCATION: (1)..(2)
<223> OTHER INFORMATION: Xaa is either Ile, Leu, Val, Phe, Tyr, Trp, or
      Met
<220> FEATURE:
<221> NAME/KEY: VARIANT
<222> LOCATION: (4)..(14)
<223> OTHER INFORMATION: at residues 4, 6, 8, 9, 11, 12, 14 Xaa is
      either Phe, or Trp
<220> FEATURE:
<221> NAME/KEY: VARIANT
<222> LOCATION: (5)..(15)
<223> OTHER INFORMATION: at residues 5 and 15  Xaa is either Arg or Lys
<220> FEATURE:
<221> NAME/KEY: VARIANT
<222> LOCATION: (16)..(20)
<223> OTHER INFORMATION: Xaa is either Phe, Trp,  Arg, Lys, or Pro
<220> FEATURE:
<221> NAME/KEY: VARIANT
<222> LOCATION: (11)..(13)
<223> OTHER INFORMATION: may be deleted
<220> FEATURE:
<221> NAME/KEY: VARIANT
<222> LOCATION: (18)..(20)
<223> OTHER INFORMATION: may be deleted

<400> SEQUENCE: 23

Xaa Xaa Pro Xaa Xaa Xaa Pro Xaa Xaa Pro Xaa Xaa Pro Xaa Xaa Xaa
1               5                  10                  15

Xaa Xaa Xaa Xaa
            20

<210> SEQ ID NO 24
<211> LENGTH: 18
<212> TYPE: PRT
<213> ORGANISM: Artificial sequence
<220> FEATURE:
<223> OTHER INFORMATION: SYNTHETIC PEPTIDE
<220> FEATURE:
<221> NAME/KEY: VARIANT
<222> LOCATION: (1)..(2)
<223> OTHER INFORMATION: Xaa is either Ile, Leu, Val, Phe, Tyr, Trp, or
      Met
<220> FEATURE:
<221> NAME/KEY: VARIANT
<222> LOCATION: (4)..(16)
<223> OTHER INFORMATION: residues 4 and 16 Xaa is either Trp or Phe
<220> FEATURE:
<221> NAME/KEY: VARIANT
<222> LOCATION: (5)..(18)
<223> OTHER INFORMATION: residues 5, 17 and 18; Xaa is either Arg or Lys
<220> FEATURE:
<221> NAME/KEY: VARIANT
<222> LOCATION: (6)..(6)
<223> OTHER INFORMATION: Xaa is either Trp or Lys
<220> FEATURE:
<221> NAME/KEY: VARIANT
<222> LOCATION: (7)..(14)
<223> OTHER INFORMATION: Xaa is either Phe, Trp, Arg, Lys, or Pro
<220> FEATURE:
<221> NAME/KEY: VARIANT
<222> LOCATION: (7)..(14)
<223> OTHER INFORMATION: may be deleted

<400> SEQUENCE: 24

Xaa Xaa Pro Xaa Xaa Xaa Xaa Xaa Xaa Xaa Xaa Xaa Xaa Xaa Pro Xaa
1               5                  10                  15

Xaa Xaa
```

```
<210> SEQ ID NO 25
<211> LENGTH: 17
<212> TYPE: PRT
<213> ORGANISM: Artificial sequence
<220> FEATURE:
<223> OTHER INFORMATION: SYNTHETIC PEPTIDE
<220> FEATURE:
<221> NAME/KEY: VARIANT
<222> LOCATION: (1)..(2)
<223> OTHER INFORMATION: Xaa is either Ile, Leu, Val, Phe, Tyr, Trp, or
      Met
<220> FEATURE:
<221> NAME/KEY: VARIANT
<222> LOCATION: (7)..(12)
<223> OTHER INFORMATION: residues 7, 9, 10, and 12; Xaa is either Trp
      or Phe
<220> FEATURE:
<221> NAME/KEY: VARIANT
<222> LOCATION: (3)..(6)
<223> OTHER INFORMATION: residues3 and 6; Xaa is either Arg or Lys
<220> FEATURE:
<221> NAME/KEY: VARIANT
<222> LOCATION: (8)..(17)
<223> OTHER INFORMATION: residues 8, 11, 13, 14, 15, 16, and 17;  Xaa
      is either Phe, Trp, Arg, Lys, or Pr
<220> FEATURE:
<221> NAME/KEY: VARIANT
<222> LOCATION: (4)..(5)
<223> OTHER INFORMATION: may be deleted
<220> FEATURE:
<221> NAME/KEY: VARIANT
<222> LOCATION: (15)..(17)
<223> OTHER INFORMATION: may be deleted

<400> SEQUENCE: 25

Xaa Xaa Xaa Pro Trp Xaa Xaa Xaa Xaa Xaa Xaa Xaa Xaa Xaa Xaa Xaa
1               5                   10                  15

Xaa

<210> SEQ ID NO 26
<211> LENGTH: 18
<212> TYPE: PRT
<213> ORGANISM: Artificial sequence
<220> FEATURE:
<223> OTHER INFORMATION: SYNTHETIC PEPTIDE
<220> FEATURE:
<221> NAME/KEY: VARIANT
<222> LOCATION: (1)..(2)
<223> OTHER INFORMATION: Xaa is either Ile, Leu, Val, Phe, Tyr, Trp, or
      Met
<220> FEATURE:
<221> NAME/KEY: VARIANT
<222> LOCATION: (5)..(13)
<223> OTHER INFORMATION: residues 5, 7, 8, 10, 11, and 13: Xaa is either
      Trp or Phe
<220> FEATURE:
<221> NAME/KEY: VARIANT
<222> LOCATION: (3)..(4)
<223> OTHER INFORMATION: Xaa is either Arg or Lys
<220> FEATURE:
<221> NAME/KEY: VARIANT
<222> LOCATION: (14)..(18)
<223> OTHER INFORMATION: Xaa is either Phe, Trp, Arg, Lys, or Pro
<220> FEATURE:
<221> NAME/KEY: VARIANT
<222> LOCATION: (10)..(12)
<223> OTHER INFORMATION: may be deleted
<220> FEATURE:
<221> NAME/KEY: VARIANT
<222> LOCATION: (15)..(18)
<223> OTHER INFORMATION: may be deleted
```

-continued

```
<400> SEQUENCE: 26

Xaa Xaa Xaa Xaa Xaa Pro Xaa Xaa Pro Xaa Xaa Pro Xaa Xaa Xaa Xaa
1               5                   10                  15

Xaa Xaa

<210> SEQ ID NO 27
<211> LENGTH: 12
<212> TYPE: PRT
<213> ORGANISM: Artificial sequence
<220> FEATURE:
<223> OTHER INFORMATION: SYNTHETIC PEPTIDE

<400> SEQUENCE: 27

Ile Leu Lys Lys Trp Pro Trp Trp Arg Trp Arg Arg
1               5                   10

<210> SEQ ID NO 28
<211> LENGTH: 13
<212> TYPE: PRT
<213> ORGANISM: Artificial sequence
<220> FEATURE:
<223> OTHER INFORMATION: SYNTHETIC PEPTIDE

<400> SEQUENCE: 28

Ile Leu Lys Lys Phe Pro Phe Phe Pro Phe Arg Arg Lys
1               5                   10

<210> SEQ ID NO 29
<211> LENGTH: 13
<212> TYPE: PRT
<213> ORGANISM: Artificial sequence
<220> FEATURE:
<223> OTHER INFORMATION: SYNTHETIC PEPTIDE

<400> SEQUENCE: 29

Ile Leu Lys Lys Phe Pro Phe Phe Pro Phe Lys Lys Lys
1               5                   10

<210> SEQ ID NO 30
<211> LENGTH: 13
<212> TYPE: PRT
<213> ORGANISM: Artificial sequence
<220> FEATURE:
<223> OTHER INFORMATION: SYNTHETIC PEPTIDE

<400> SEQUENCE: 30

Ile Leu Lys Lys Trp Ala Trp Trp Pro Trp Arg Arg Lys
1               5                   10

<210> SEQ ID NO 31
<211> LENGTH: 13
<212> TYPE: PRT
<213> ORGANISM: Artificial sequence
<220> FEATURE:
<223> OTHER INFORMATION: SYNTHETIC PEPTIDE

<400> SEQUENCE: 31

Ile Leu Lys Lys Trp Pro Trp Trp Ala Trp Arg Arg Lys
1               5                   10

<210> SEQ ID NO 32
<211> LENGTH: 13
<212> TYPE: PRT
<213> ORGANISM: Artificial sequence
<220> FEATURE:
<223> OTHER INFORMATION: SYNTHETIC PEPTIDE
```

<400> SEQUENCE: 32

Ile Leu Lys Lys Trp Pro Trp Trp Pro Trp Lys Lys Lys
1               5                   10

<210> SEQ ID NO 33
<211> LENGTH: 13
<212> TYPE: PRT
<213> ORGANISM: Artificial sequence
<220> FEATURE:
<223> OTHER INFORMATION: SYNTHETIC PEPTIDE

<400> SEQUENCE: 33

Ile Leu Arg Arg Trp Pro Trp Trp Pro Trp Arg Arg Arg
1               5                   10

<210> SEQ ID NO 34
<211> LENGTH: 13
<212> TYPE: PRT
<213> ORGANISM: Artificial sequence
<220> FEATURE:
<223> OTHER INFORMATION: SYNTHETIC PEPTIDE

<400> SEQUENCE: 34

Trp Trp Lys Lys Trp Pro Trp Trp Pro Trp Arg Arg Lys
1               5                   10

<210> SEQ ID NO 35
<211> LENGTH: 13
<212> TYPE: PRT
<213> ORGANISM: Artificial sequence
<220> FEATURE:
<223> OTHER INFORMATION: SYNTHETIC PEPTIDE

<400> SEQUENCE: 35

Phe Phe Lys Lys Trp Pro Trp Trp Pro Trp Arg Arg Lys
1               5                   10

<210> SEQ ID NO 36
<211> LENGTH: 13
<212> TYPE: PRT
<213> ORGANISM: Artificial sequence
<220> FEATURE:
<223> OTHER INFORMATION: SYNTHETIC PEPTIDE

<400> SEQUENCE: 36

Phe Phe Lys Lys Phe Pro Phe Phe Pro Phe Arg Arg Lys
1               5                   10

<210> SEQ ID NO 37
<211> LENGTH: 13
<212> TYPE: PRT
<213> ORGANISM: Artificial sequence
<220> FEATURE:
<223> OTHER INFORMATION: SYNTHETIC PEPTIDE

<400> SEQUENCE: 37

Phe Phe Lys Lys Phe Pro Phe Phe Pro Phe Lys Lys Lys
1               5                   10

<210> SEQ ID NO 38
<211> LENGTH: 16
<212> TYPE: PRT
<213> ORGANISM: Artificial sequence
<220> FEATURE:
<223> OTHER INFORMATION: SYNTHETIC PEPTIDE

<400> SEQUENCE: 38

Ile Leu Lys Lys Trp Pro Trp Trp Pro Trp Trp Pro Trp Arg Arg Lys
1               5                   10                  15

<210> SEQ ID NO 39
<211> LENGTH: 15
<212> TYPE: PRT
<213> ORGANISM: Artificial sequence
<220> FEATURE:
<223> OTHER INFORMATION: SYNTHETIC PEPTIDE

<400> SEQUENCE: 39

Ile Leu Lys Lys Trp Pro Trp Trp Pro Trp Arg Trp Trp Arg Arg
1               5                   10                  15

<210> SEQ ID NO 40
<211> LENGTH: 15
<212> TYPE: PRT
<213> ORGANISM: Artificial sequence
<220> FEATURE:
<223> OTHER INFORMATION: SYNTHETIC PEPTIDE

<400> SEQUENCE: 40

Ile Leu Lys Lys Trp Pro Trp Trp Pro Trp Arg Arg Trp Trp Lys
1               5                   10                  15

<210> SEQ ID NO 41
<211> LENGTH: 15
<212> TYPE: PRT
<213> ORGANISM: Artificial sequence
<220> FEATURE:
<223> OTHER INFORMATION: SYNTHETIC PEPTIDE

<400> SEQUENCE: 41

Ile Leu Lys Lys Trp Pro Trp Trp Pro Trp Pro Pro Arg Arg Lys
1               5                   10                  15

<210> SEQ ID NO 42
<211> LENGTH: 17
<212> TYPE: PRT
<213> ORGANISM: Artificial sequence
<220> FEATURE:
<223> OTHER INFORMATION: SYNTHETIC PEPTIDE

<400> SEQUENCE: 42

Ile Leu Lys Lys Trp Pro Trp Trp Pro Trp Pro Phe Phe Arg Arg
1               5                   10                  15

Lys

<210> SEQ ID NO 43
<211> LENGTH: 17
<212> TYPE: DNA
<213> ORGANISM: Artificial sequence
<220> FEATURE:
<223> OTHER INFORMATION: PCR primer

<400> SEQUENCE: 43
gcatatcgaa ttccatg                                                17

<210> SEQ ID NO 44
<211> LENGTH: 16
<212> TYPE: DNA
<213> ORGANISM: Artificial sequence

```
<220> FEATURE:
<223> OTHER INFORMATION: PCR primer

<400> SEQUENCE: 44
ctgcaggtcg acgagc                                                     16
```